United States Patent
Kariman (10) Patent No.: US 10,307,392 B2
(45) Date of Patent: Jun. 4, 2019

(54) COMPOUND AND METHOD FOR TREATMENT OF DISEASES AND DISORDERS

(71) Applicant: Alexander Kariman, Rockville, MD (US)

(72) Inventor: Alexander Kariman, Rockville, MD (US)

( * ) Notice: Subject to any disclaimer, the term of this patent is extended or adjusted under 35 U.S.C. 154(b) by 0 days.

(21) Appl. No.: 15/789,998

(22) Filed: Oct. 21, 2017

(65) Prior Publication Data

US 2019/0117617 A1    Apr. 25, 2019

(51) Int. Cl.
*A61K 31/353* (2006.01)
*A61K 31/352* (2006.01)
*A61K 36/185* (2006.01)
*A61K 31/05* (2006.01)

(52) U.S. Cl.
CPC ............ *A61K 31/352* (2013.01); *A61K 31/05* (2013.01); *A61K 36/185* (2013.01)

(58) Field of Classification Search
CPC .................................................. A61K 31/353
USPC ......................................................... 514/454
See application file for complete search history.

(56) References Cited

U.S. PATENT DOCUMENTS

| 2010/0216872 | A1* | 8/2010 | Letzel | A61K 36/185 514/454 |
| 2015/0086494 | A1* | 3/2015 | Sekura | A61K 36/00 424/59 |
| 2016/0101063 | A1* | 4/2016 | Yeshurun | A61K 31/573 514/729 |
| 2016/0279077 | A1* | 9/2016 | De Vries | A61K 9/2018 |
| 2018/0236017 | A1* | 8/2018 | Stoops | A61K 36/185 |

* cited by examiner

*Primary Examiner* — Raymond J Henley, III (57) ABSTRACT

The disclosed invention generally relates to treatment and/or prevention of symptoms associated with cannabinoid responsive diseases and disorders in subjects in need thereof, as well as the method of administering therapeutically-effective amount of a pharmaceutical compound containing cannabinoids. The disclosed invention further relates to pharmaceutical compounds for treating and/or preventing symptoms associated with said diseases and disorders.

27 Claims, 3 Drawing Sheets

COMPOUND AND METHOD FOR TREATMENT OF DISEASES AND DISORDERS

FIELD OF THE INVENTION

The present invention relates to pharmaceutical compounds and methods for treating and/or preventing symptoms associated with cannabinoid responsive diseases and disorders, such as multiple sclerosis (MS), and to pharmaceutical compounds and methods for treating and/or preventing symptoms associated with said diseases and disorders.

BACKGROUND OF THE INVENTION

Cannabinoid components of marijuana are known to exert behavioral and psychotropic effects but also to possess therapeutic properties including analgesia, ocular hypotension, and antiemesis. Cannabinoids-based medications are now being used for treatment of a wide range of medical conditions, including neuropathic pain, pain related to cancer and trauma, spasticity associated with multiple sclerosis, fibromyalgia, and others. This invention generally relates to treatment of symptoms associated with cannabinoid responsive diseases and disorders in subjects in need thereof, as well as the method of administering therapeutically-effective amount of a pharmaceutical compound containing cannabinoids.

The methods and compounds of the proposed invention are intended for treatment of multiple diseases and disorders such as, without limitation: autoimmune diseases and disorders, motor neuron diseases and disorders, neurodegenerative diseases and disorders, pain associated with cancer and trauma.

Other conditions are also contemplated by the invention, that include, but are not limited to: gastrointestinal, metabolic, neurological, circulatory, soft tissue, musculoskeletal, chronic or acute pain, nausea, decreased appetite, skin disorders, sexual dysfunction, glaucoma, AIDS wasting, neuropathic pain, treatment of spasticity associated with multiple sclerosis, fibromyalgia, chemotherapy-induced nausea, allergies, inflammation, infection, epilepsy, depression, migraine, bipolar disorders, anxiety disorder, dependency and withdrawal. In addition, the methods of the invention may be used to alleviate, or relief symptoms or side effects associated with anti-retroviral therapy, chemotherapy and radiation therapy. Certain diseases and disorders are briefly outlined below, and the possible mechanisms of cannabinoid action are exemplified with treatment of certain autoimmune neurodegenerative diseases.

An autoimmune disease develops when person's immune system, which defends the body against diseases starts attacking the healthy cells. An autoimmune disease can affect one or many different types of body tissue, depending on the type. It can also cause abnormal organ growth and changes in organ function. The cause of autoimmune disease is currently unknown.

There are as many as 80 types of autoimmune diseases. Many of them have similar symptoms, which makes them difficult to diagnose. It's also possible to have more than one disease at the same time. Autoimmune diseases usually fluctuate between periods of remission (few or no symptoms) and flare-ups (worsening symptoms). Currently, treatments for autoimmune diseases focused on relieving symptoms and preventing complications because there is no curative therapy. Medical interventions include: physical therapy, immunosuppressive medication, hormone replacement therapy, blood transfusions (if blood is affected), anti-inflammatory medication, pain medication, etc.

For example, multiple sclerosis (MS) is believed to be an autoimmune disease that affects the central nervous system (CNS). The CNS consists of the brain, spinal cord, and the optic nerves. Surrounding and protecting the nerve fibers of the CNS is a fatty tissue called myelin that helps nerve fibers conduct electrical impulses. In MS, myelin is lost in multiple areas, leaving scar tissue called sclerosis. These damaged areas are also known as plaques or lesions. In some cases, the nerve fiber itself is damaged or broken. When myelin or the nerve fiber is destroyed or damaged, the ability of the nerves to conduct electrical impulses to and from the brain is disrupted, and this produces the various symptoms of MS. Patients with MS can expect one of four clinical courses of disease: relapsing-remitting, primary-progressive, secondary-progressive or progressive-relapsing.

Neurodegenerative diseases, such as MS, are a group of disorders characterized by changes in normal neuronal functioning, leading, in most cases, to neuronal death. Most of these diseases are associated, especially in late stages, with severe neuronal loss. With an ever-increasing ageing population, progressively more individuals are affected by neurodegenerative diseases. According to the National Institute of Neurological Disorders and Stroke, there are more than 600 different types of neurological disorders.

Neural degeneration, or neurodegeneration, can be described as the progressive damage or death of neurons. Neurons are nerve cells in the brain whose primary function is to assist in the memory process. The damage or death of neurons leads to a gradual deterioration of the functions controlled by the affected part of the nervous system. Neural degeneration often occurs because of oxidative stress. Oxidative stress occurs to the cells when the effects of pro-oxidants (such as free radicals, reactive oxygen and reactive nitrogen species) exceed the ability of anti-oxidants to neutralize them. When levels of free radicals or other pro-oxidants increase to such an extent, they can cause damage to cell membranes which in turn may result in cell death or damage to genetic material.

Some of the most common types of neurological disorders include Alzheimer's disease, Parkinson's disease and MS. The process of neural degeneration is often the result of glutamate excitotoxicity. Glutamate is a signaling chemical and under normal conditions the concentration of glutamate in a cell tends to be quite low. Glutamate is required at these low concentrations for crucial brain functions such as memory and learning. When glutamate concentrations increase, the process of neural degeneration begins.

When the brain is deprived of oxygen either due to a disease, such as a neurogenerative disease, a trauma, such as a closed head injury or due to an ischemic event such as a stroke, an abnormal build-up of glutamate occurs. Neural degeneration takes place when glutamate attaches to receptor proteins on a cells surface. Neural degeneration continues from the destructive effects of oxidative radicals caused by the glutamate flood. The radicals cause disruption of essential reactions in the neurons and this leads to degeneration or death of the cell.

Neuroprotective agents that can block the NMDA receptor are useful as they are able to block the reaction caused by glutamate and therefore prevent neural degeneration. Some neuroprotective agents, which block the NMDA receptor, have been studied in clinical trials in stroke patients. Dextrorphan was the first NMDA antagonist to be studied in human subjects but is of limited use due to its side effects. Another drug, Selfotel, showed trends towards a higher mortality rate with patients treated with the drug rather than placebo, and as such the trials were halted. The drug Cerestat also had its trials terminated because of concerns with the benefit-to-risk ratio of the drug.

The motor neuron diseases (MNDs) are a group of progressive neurological disorders that destroy motor neurons, the cells that control essential voluntary muscle activity such as speaking, walking, breathing, and swallowing. Normally, messages from nerve cells in the brain (called upper motor neurons) are transmitted to nerve cells in the brain stem and spinal cord (called lower motor neurons) and from them to muscles. Upper motor neurons direct the lower motor neurons to produce movements such as walking or chewing. Lower motor neurons control movement in the arms, legs, chest, face, throat, and tongue.

When there are disruptions in the signals between the lowest motor neurons and the muscle, the muscles do not work properly; the muscles gradually weaken and may begin wasting away and develop uncontrollable twitching (fasciculations). After there are disruptions in the signals between the upper motor neurons and the lower motor neurons, the limb muscles develop stiffness (spasticity), movements become slow and effortful, and tendon reflexes such as knee and ankle jerks become overactive. Over time, the ability to control voluntary movement can be lost. Some MNDs are inherited, but the causes of most MNDs are not known. In sporadic or non-inherited MNDs, environmental, toxic, viral, or genetic factors may be implicated. Amyotrophic lateral sclerosis (ALS), progressive bulbar palsy, pseudobulbar palsy, primary lateral sclerosis (PLS), progressive muscular atrophy, spinal muscular atrophy (SMA), post-polio syndrome (PPS) are among the frequently encountered MNDs.

Amyotrophic lateral sclerosis is an MND that affects over 350,000 of the world's population and kills over 100,000 every year. Early symptoms associated with ALS include tripping, dropping things, slurred or "thick" speech, and muscle cramping, stiffening, weakening, and twitching (fasciculation). In bulbar ALS, the muscles for speaking, swallowing or breathing are affected. In addition to muscle loss atrophy, the following signs of lower and upper motor neuron degeneration are often associated with ALS lower motor neuron degeneration: muscle weakness and atrophy, involuntary contraction of muscle fibers, muscle cramps, weakened reflexes, flaccidity (decreased muscle tone), difficulty swallowing, disordered articulation, shortness of breath at rest, etc. Upper motor neuron degeneration: muscle stiffness or rigidity, emotional lability (decreased ability to control emotions).

Significant advances are being made towards understanding the genetic basis for ALS as well as the mechanistic and molecular pathways mediating progression of the sporadic forms of the disease, however, effective pharmacotherapy remains elusive. Two of the primary theories underlying motor neuron vulnerability are susceptibility to excitotoxicity and oxidative damage.

The use of *cannabis* as a medicine has long been known and during the 19$^{th}$ century preparations of *cannabis* were recommended as a hypnotic sedative which were useful for the treatment of hysteria, delirium, epilepsy, nervous insomnia, migraine, pain and dysmenorrhea. Until recently the administration of *cannabis* to a patient was mainly achieved by preparation of *cannabis* by decoction in ethanol, which could then be swallowed or by the patient inhaling the vapors of *cannabis* by smoking the dried plant material.

Recent methods have sought to find new ways to deliver cannabinoids to a patient including those which bypass the stomach and the associated first pass effect of the liver which can remove up to 90% of the active ingested dose and avoid the patient having to inhale unhealthy tars and associated carcinogens into their lungs. Such dosage forms include administering the cannabinoids to the sublingual or buccal mucosae, inhalation of a cannabinoid vapor by vaporization or nebulization, enemas or solid dosage forms such as gels, capsules, tablets, pastilles and lozenges.

Cannabinoids are a group of chemicals known to activate cannabinoid receptors in cells. These chemicals, which are found in *cannabis* plants, are also produced endogenously in humans and other animals, these are termed endocannabinoids. Synthetic cannabinoids are chemicals with similar structures to plant cannabinoids or endocannabinoids. Plant cannabinoids can also be isolated such that they are "essentially pure" compounds. These isolated cannabinoids are essentially free of the other naturally occurring compounds, such as, other minor cannabinoids and molecules such as terpenes.

The U.S. Pat. No. 7,449,589, referenced herein, demonstrates one of many processes for purifying (−)-Δ9-trans-tetrahydrocannabinol and shows various cannabinoid compounds, including THC, CBD, and CBN. The THC reportedly has at least eight individual isomers of which (−)-Δ9-trans-tetrahydrocannabinol ((−)-Δ9-trans-THC) is the main and most active isomer. Although Δ8-tetrahydrocannabinol has similar activity as (−)-Δ9-trans-THC, it is only approximately 75% as potent and also tends to degrade to other compounds including CBN. (U.S. Pat. No. 7,449,589 B2, 2004)

Essentially pure compounds have a degree of purity up to at least 95% by total weight. Some essentially pure cannabinoids (whether synthetic or isolated) have been suggested to be neuroprotective agents, either by direct antagonism of the NMDA receptor or by reducing the influx of calcium ions into the cell by another means such as binding with cannabinoid receptors. Clearly there is a significant requirement for an efficacious NMDA antagonist to prevent or treat neural degeneration.

It was discovered that glutamate toxicity could be prevented to some extent by isolated or synthetic tetrahydrocannabinol (THC) or cannabidiol (CBD). (Hampson, Grimaldi, Axelrod, & Wink, 1998) The cannabinoids were tested in vitro on neuronal cultures exposed to glutamate. Cannabidiol (CBD) and other cannabinoids were examined as neuroprotectants in rat cortical neuron cultures exposed to toxic levels of the neurotransmitter, glutamate.

According to one study, the psychotropic cannabinoid receptor agonist delta 9-tetrahydrocannabinol (THC) and cannabidiol (CBD), a non-psychoactive constituent of marijuana, both reduced NMDA, AMPA and kainate receptor mediated neurotoxicity. Neuroprotection was not affected by cannabinoid receptor antagonist, indicating a (cannabinoid) receptor-independent mechanism of action. (Hampson, et al., 2000)

Glutamate toxicity can be reduced by antioxidants. Using cyclic voltametry and a fenton reaction-based system, it was demonstrated that cannabidiol (CBD), THC and other cannabinoids are potent antioxidants. As evidence that cannabinoids can act as antioxidants in neuronal cultures, cannabidiol (CBD) was demonstrated to reduce hydroperoxide toxicity in neurons. In a head to head trial of the abilities of various antioxidants to prevent glutamate toxicity, cannabidiol was superior to both alpha-tocopherol and ascorbate in protective capacity. Recent preliminary studies in a rat model of focal cerebral ischemia suggest that cannabidiol (CBD) may be at least as effective in vivo as seen in these in vitro studies. (Hampson, et al., 2000)

Figure 2:
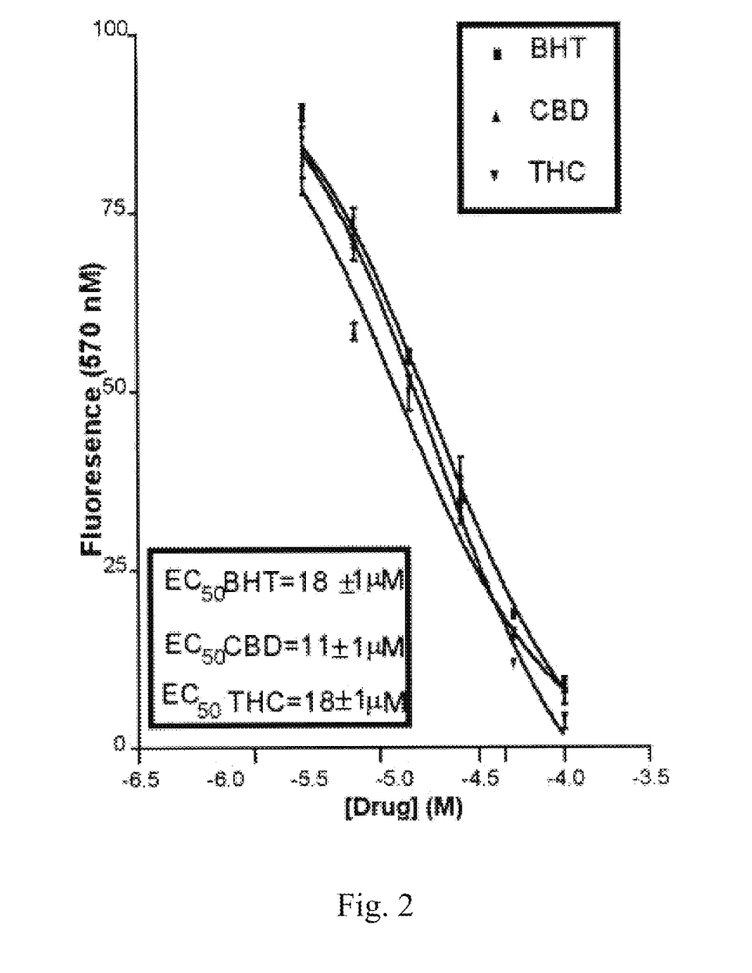

The example illustrated in the FIG. 2, incorporated herein by reference, compares the oxidation potentials of cannabinoids and the antioxidant butylated hydroxytoluene (BHT). Effect of cannabidiol and THC on dihydrorhodamine oxidation. Cannabinoids were compared with BHT for their ability to prevent tert-butyl hydroperoxide-induced oxidation of dihydrorhodamine. This experiment was repeated four times with essentially the same results. (Hampson, Grimaldi, Axelrod, & Wink, 1998)

Figure 1:
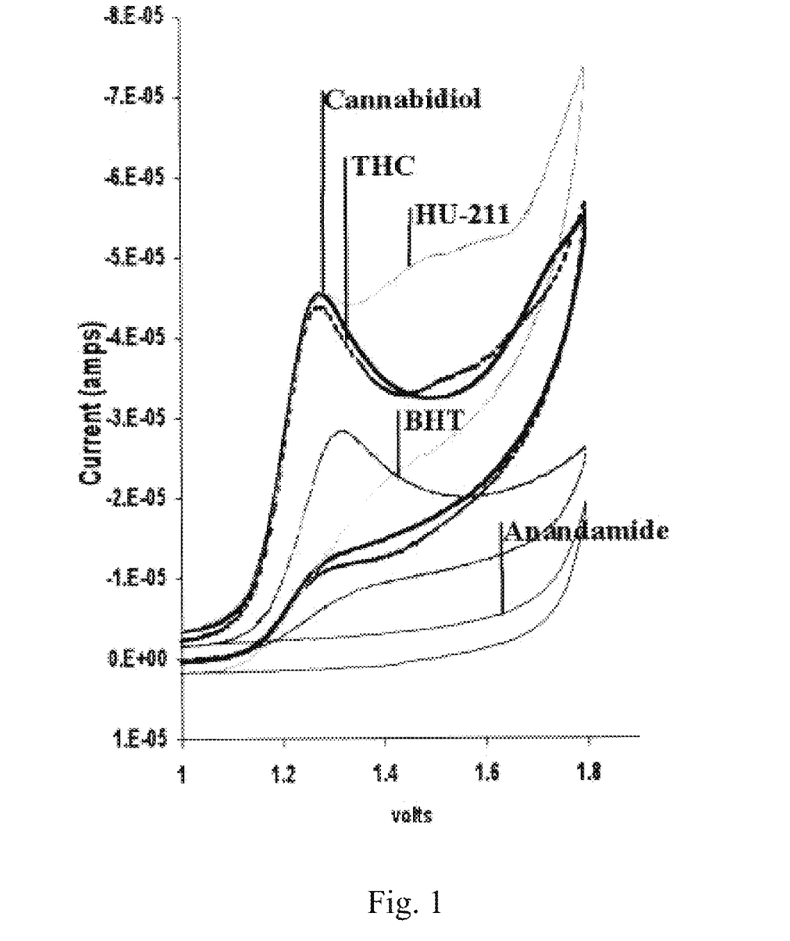

In 1988 a study was undertaken to determine the analgesic and anti-inflammatory activity of various cannabinoids and cannabinoid pre-cursors. Oral administration of CBD was found to be the most effective at inhibition of PBQ-induced writhing in mice. THC and cannabinol (CBN) were found to be least effective at reducing analgesia and inflammation. (Formukong, Evans, & Evans, 1988) Another study undertaken in 1998, as demonstrated in the FIG. 1, incorporated herein by reference, compares the oxidation potentials of cannabinoids and the antioxidant butylated hydroxytoluene (BHT).

Further, certain anecdotic evidence suggests that cannabinoid-containing plant extracts are demonstrating higher efficacy in treatment of some neurodegenerative diseases than essentially pure cannabinoids. Specifically, cannabinoid-containing plant extracts comprising, as a predominant cannabinoid, tetrahydrocannabinol (THC) and cannabidiol (CBD)—particularly effective in the retardation of neural degeneration.

Several pharmaceutical products exist which contain either phytocannabinoids (natural) or synthetic cannabinoids. For example, dronabinol (Marinol) is the International Nonproprietary Name (INN) for an encapsulated THC product which has been used therapeutically as an appetite stimulant, antiemetic, and analgesic, either as an inhalant or as an oral drug. Also, nabilone (Cesamet) is a synthetic analog of dronabinol (Marinol), while Sativex is a cannabinoid extract oral spray containing THC, and other cannabinoids that are used to treat neuropathic pain and spasticity. Further, rimonabant (marketed under various tradenames) is a selective cannabinoid receptor antagonist used as an anti-obesity drug and as a smoking cessation. Several other cannabinoid-containing products exist.

Thus, considering the therapeutic effect of compounds containing cannabinoids, especially $(-)-\Delta^9$-trans-THC, there is a continuing need for improving existing cannabinoid-containing products as well as a need for new products containing cannabinoids, especially in the pharmaceutical field.

The U.S. Pat. No. 8,628,796, referenced herein, discloses an encapsulated THC composition, including $(-)-\Delta9$-trans-THC purportedly having improved stability. The disclosure emphasizes that the stability can be improved by including bases (e.g., amines) in the formulation. In addition, the stability of the compositions disclosed is best preserved by storing the compositions in a sealed container, such as in a capsule, and under refrigerated conditions. Specifically, the disclosure asserts that one embodiment of the invention described therein overcomes the deficiencies of prior art oral dosage forms containing $(-)-\Delta9$-trans-THC by utilizing hard gelatin capsules, instead of soft gelatin capsules. As stated in the disclosure, unlike soft gelatin capsules, hard gelatin capsules do not contain glycerol—a major cause of instability for the active $(-)-\Delta9$-trans-THC pharmaceutical ingredient. The disclosure purports to provide a stable product, such as one that does not degrade to an unacceptable extent during the desired shelf-life of the dosage form. (U.S. Pat. No. 8,628,796 B2, 2005)

The U.S. Pat. No. 7,968,594, referenced herein, discloses the invention that relates to treatment of cancer related pain and constipation. The subject in need is administered a combination of the cannabinoids cannabidiol (CBD) and delta-9-tetrahydrocannabinol (THC) in a predefined ratio by weight of approximately 1:1 of CBD to THC. (U.S. Pat. No. 7,968,594 B2, 2005)

The U.S. Pat. No. 9,205,063, referenced herein, discloses the invention that relates to the use of cannabinoid-containing plant extracts in the prevention or treatment of neural degeneration. Specifically, the invention relates to use of one or more cannabinoid-containing plant extracts in the prevention or treatment of neural degeneration, wherein the one or more cannabinoid-containing plant extracts comprise a cannabinoid-containing fraction and a non-cannabinoid containing fraction. (U.S. Pat. No. 9,205,063 B2, 2014)

The U.S. Pat. Application No. 20,140,228,438, referenced herein, discloses the invention that relates to cannabinoids for use in the prevention or treatment of neurodegenerative diseases or disorders. Preferably, the cannabinoids are cannabichromene (CBC) cannabidivarin (CBDV) and/or cannabidivarin acid (CBDVA). More preferably, the neurodegenerative disease or disorder to be prevented or treated is Alzheimer's disease. (US Patent No. US20140228438 A1, 2012)

The U.S. Pat. Application No. 20,060,135,599, referenced herein, discloses the invention that relates to the use of one or more cannabinoids in the treatment of neuropathic or chronic pain. A method of treating brachial plexus avulsion in a human patient comprising administering to a patient in need thereof effective amount one or more cannabinoids. (US Patent No. US20060135599 A1, 2003)

The U.S. Pat. No. 8,980,940, referenced herein, discloses a composition comprising a high purity cannabinoid, an acid, and a pharmaceutically-acceptable solvent that achieves room temperature stability for over 24 months. The acid improves the stability of the composition and the solvent enhances the solubility of the acid, thereby allowing the acid to have an improved stabilizing effect on the highly pure cannabinoid. Preferably, the solvent is an alcohol and, more preferably, the composition contains an oil. A method for making the composition includes combining the cannabinoid and the solvent and evaporating a portion of the solvent, along with adding an acid to the composition, before, during, or after the evaporating step. A method for making and storing the composition includes storing the composition in a manner adapted to maintain its stability. (U.S. Pat. No. 8,980,940 B2, 2011)

The U.S. Pat. Application No. 20,080,175,902, referenced herein, discloses methods for slowing the progression of multiple sclerosis comprising administering a therapeutically effective amount of a cannabinoid to a patient suffering from multiple sclerosis. A method of slowing the progression of multiple sclerosis in a patient in need thereof, comprising administration of a pharmaceutical composition containing an effective amount of therapeutically effective cannabinoid on a regular basis; the administration occurring over a period of time: at least about 16 weeks, at least about 27 weeks, at least about 40 weeks and at least about 52 weeks. (US Patent No. US20080175902 A1, 2007)

The U.S. Pat. Application No. 20,060,167,084, referenced herein, discloses methods of, inter alia, treating and/or preventing symptoms associated with multiple sclerosis and its relapse. A method of treating and/or preventing symptoms associated with multiple sclerosis in a subject in need thereof, the method comprising administering to the subject a therapeutically effective amount of a pharmaceutical composition comprising delta-9-tetrahydrocannabinol. (US Patent No. US20060167084 A1, 2005)

The U.S. Pat. Application No. 20,040,018,151, referenced herein, discloses in one aspect, a method for promoting normal motor function in ALS patients. The method comprises administering a compound that is an anandamide/cannabinoid receptor/acceptor agonist to a mammal having observable motor function and evaluating one or more indicia of motor function in said mammal, wherein a compound that promotes normal motor function is identified. More preferably, the mammal to which the administration is made has one or more ALS or MND symptoms and such one or more symptoms include at least one of the observable motor functions being evaluated. (US Patent No. US20040018151 A1, 2003)

SUMMARY OF THE INVENTION

The following description presents a simplified view of one or more aspects of the proposed invention. This summary is not an extensive overview of all contemplated embodiments and implementations. It is intended to neither identify key or critical elements of all features, nor delineate the scope of any or all facets. Its sole purpose is to present some concepts of one or more aspects in a simplified form.

A cannabinoid-containing plant extract contains in addition to one or more other cannabinoids, one or more non-cannabinoid components which are co-extracted with the cannabinoids from the plant material. Their respective ranges will vary according to the starting plant material and the extraction methodology used. Cannabinoid-containing plant extracts may be obtained by various means of extraction of *cannabis* plant material. Such means include but are not limited to: supercritical or subcritical extraction with $CO2$, extraction with hot gas, and extraction with solvents. The term "cannabinoid-containing plant extract" is taken herein to refer to one or more plant extracts from the *cannabis* plant.

It was discovered, that the use of *cannabis*-based extracts that contain THC and CBD in the ratio of approximately 1 (THC) and 2 (CBD) by mass, or THC and CBD in the ratio of 0.5 to 1 (THC) and 1.5 to 2 (CBD) by mass, or THC and CBD in the ratio of 1 to 1.5 (THC) and 2 to 2.5 (CBD) by mass, and contain one or more other cannabinoids or non-cannabinoid components co-extracted with cannabinoids from the plant material is more effective for a symptomatic treatment of the following ailments than a compound where the amount of THC exceeds the amount of CBD (for instance, an ex-US drug nabiximols (Sativex) (botanical THC/CBD combination)): autoimmune diseases and disorders, motor neuron diseases and disorders, neurodegenerative diseases and disorders, as well as pain associated with cancer and trauma.

It was also discovered that certain unwanted side effects caused by current medications, are reduced or eliminated when treating patients with the compounds disclosed herein. One major side effect of the currently used medications containing THC (or its analogs), such as a US-listed drug dronabinol (Marinol) (synthetic THC) or Sativex, is the debilitating psychotropic effect at higher therapeutic doses. The higher doses are often necessary for resistant patients to manage pain, depression, or motoric disfunctions associated with: neuropathic pain, such as allodynia in Complex Regional Pain Syndrome (CRPS), MS spasticity, Spinal Cord Injury (SCI)-related spasticity, Hereditary Spastic Paraplegia (HSP)-related spasticity, Spastic Diplegia Cerebral Palsy (SDCP)-related spasticity, Spinocerebellar Ataxias (SA)-related spasticity, Huntington's Disease (HD) chorea, Post Traumatic Stress Disorder (PTSD) depression, Tuberous Sclerosis (TS) tumors and inflammation, and others.

Neurodegenerative diseases, such as MS, are characterized by changes in normal neuronal functioning, leading, in most cases, to neuronal death (Rudroff & Honce, 2017). Studies in animals and humans demonstrate that changes also occur in the endocannabinoid system (Leussink, et al., 2012). More specifically, multiple studies indicate that control of spasticity in MS is mediated by CB1, and not CB2 cannabinoid receptors, but the role of CB2 receptor cannot be entirely excluded (Pryce & Baker, 2007).

There are multiple studies demonstrating spasticity inhibition of THC—the main psychotropic constituent of the *Cannabis sativa* plant (Malfitano, Proto, & Bifulco, 2008) (Petro & Ellenberger, Treatment of human spasticity with delta 9-tetrahydrocannabinol, 1981) (Ungerleider, Andyrsiak, Fairbanks, Ellison, & Myers, Delta-9-THC in the treatment of spasticity associated with multiple sclerosis, 1987). Also, a synthetic THC drug Marinol (United Pharmaceuticals) and THC derived Cesamet (Valeant Pharmaceuticals International) were tested and both demonstrated positive results in reducing spasticity (Leussink, et al., 2012). This is not surprising since THC is a CB1 and CB2 receptor partial agonist (Pertwee, 2008). Yet, CB1 receptor also mediates the THC-induced psychoactivity (Pryce & Baker, 2007). Consequently, there is a mounting evidence of the unwanted psychotropic effects, especially with synthetic THC and natural THC at higher doses, such as intoxication, sedation, memory impairment, dysphoria (Russo & Guy, 2006) and adverse behavioral changes. Russo et al., (2015) state that physicians should pay more attention when prescribing cannabinoid drugs to MS patients affected by spasticity since neurobehavioral side effects may emerge especially in predisposed individuals.

It is rather difficult to dissociate the therapeutic effects from the adverse effects of cannabinoids when using *cannabis* as a medicine. It is, however, hypothesized that this aspect can be mitigated by administering a *cannabis* extract that contains other cannabinoids in addition to THC (Russo & Guy, 2006). Cannabidiol—an antagonist of CB1 and CB2 receptors (Pertwee, 2008) is believed to be modulating the THC psychotropic effect (Russo & Guy, 2006) (Karniol, Shirakawa, Kasinski, Pfeferman, & Carlini, 1974). However, the effective concentrations and ratios, pharmacodynamics, presence or absence of other substances that facilitate this complex interaction was not understood until now.

It is plausible that CBD functions as a negative allosteric modulator by binding to a site on the CB1 receptor distinct from the THC binding site (Laprairie, Bagher, & Denovan-Wright, 2015). From this secondary site, the inventors conclude, CBD is able to change the shape of the receptor in a way that there is less THC binding and less activation of the CB1 receptor. CBD was shown to inhibit uptake and metabolism of anandamide (Kluger, Triolo, Jones, & Jankovic, 2015). It is also suggested that at low concentrations CBD acts as an inverse agonist, binding to the same receptors that other agonists do but causing a different physiological effect (Thomas, et al., 2007). Reduced THC potency was seen at CBD concentrations as low as 100 nM that is well achievable in a human (Laprairie, Bagher, & Denovan-Wright, 2015). Further, in line with classical pharmacology, the responses THC elicits appear to be strongly influenced both by the expression level and signaling efficiency of cannabinoid receptors and by ongoing endogenous cannabinoid release (Pertwee, 2008).

CBD also inhibits the conversion of THC into its particularly psychoactive metabolites 11-hydroxy-THC, reducing psychoactive effects, yet, it works synergistically with THC on control of pain and spasticity (Russo & Guy, 2006). It is further suspected that CBD delays the absorption of THC, and consequently peak serum concentrations that are associated with the occurrence of unwanted side effects are avoided (Russo & Guy, 2006). It has been further observed that *cannabis* strains, containing CBD levels equal or higher than THC, have positive effects on muscle spasticity (Rog, Nurmikko, Friede, & Young, 2005). These positive effects of *cannabis* on spasticity and pain and its safety have also been emphasized by the American Academy of Neurology (Koppel, et al., 2014). Moreover, CBD is presumed to have antipsychotic, anxiolytic, and anticonvulsant effects (Leussink, et al., 2012), and experimental evidence suggests that THC, as well as CBD, exhibit anti-inflammatory, neuroprotective (Hampson, Grimaldi, Axelrod, & Wink, 1998), and immunomodulatory properties, pointing to additive or potentiating effects of the combination of the two (Jamontt, Molleman, Pertwee, & Parsons, 2010).

Considering these unique pharmacological qualities of THC and CBD that can be further enhanced by presence of other phytochemicals, the concentrations and ratios used to date were marginally successful because of either their low efficacy at lower doses, or psychotropic or behavioral side effects at the effective doses. "There was no significant difference in NRS [Numeric Pain Scale] scores between subjects treated with nabiximols [Sativex, THC/CBD combination where THC>CBD] and placebo in two Phase 3 trials (GW Pharma Ltd, n.d.)."

Considering the known deficiencies of comparable commercial and experimental drugs, the inventor is proposing a new formulation that is potentially more effective clinically for treating pain, inflammation, mood, spasticity, and motoric symptoms associated with psychiatric, autoimmune and neurological diseases and disorders, such as, but not limited to neuropathic, acute or chronic pain such as in CPRS, cancer or trauma; Ataxias (cerebellar, sensory, vestibular), such as tremor or vertigo; MS, HSP, SCI, SDCP, SA spasticity and pain, HD chorea; PD rigidity; PTSD depression; migraine; TS tumors and inflammation-all these symptoms are responsive to specific modulations of the endocannabinoid receptors and/or the neuroprotective/antioxidant qualities of specific cannabinoids.

Though, the clinical effect of combination therapy has been confirmed in studies and commercially with Sativex (THC/CBD combination where THC>CBD), it is apparent that the total dose of THC delivered in Sativex is not sufficient to saturate the receptors, not making full use of the medication's therapeutic potential. The literature on Sativex shows a large variance in daily doses. Sativex is administered as buccal spray, from 5 sprays per day (Johnson, Lossignol, Burnell-Nugent, & Fallon, 2013) to a maximum of 14 sprays (THC 2.7 mg:CBD 2.5 mg per spray) (Bayer HealthCare press release and Medical Update Memo of Multiple Sclerosis Society of Canada, 2005). At these high doses, not surprisingly, the unwanted psychotropic effects of THC become dominant, limiting the drug's utility.

To achieve the desired efficacy attainable at high THC doses, but overcoming the negative psychotropic effect, the inventor employs a balanced THC/CBD formula that ranges in some embodiments 0.5 to 1 (THC) and 1.5 to 2 (CBD) ratios, and in other embodiments 1 to 1.8 (THC) and 2 to 2.5 (CBD) ratios (from approximately 52% to 83% of CBD, where THC and CBD is 100%) with, in one embodiment, a 190 mg maximum one-time dose, whereas CBD in the ratios significantly higher than found in Sativex (relative to THC concentrations), would limit the THC psychotropic effect. In addition, in one embodiment, the formulation contains up to 50% of the total formulation other phytochemicals and impurities co-extracted with THC and/or CBD from the *Cannabis* plant. And in another embodiment, THC and CBD represent at least 97% of the total formulation and the remaining 3% or less are impurities.

Considering the safety aspects associated with higher THC and CBD doses, the inventor believes, and it was experimentally determined in humans and animals, that aforesaid formulations and dosing is appropriate for patients, which is in addition corroborated by the following experiments with higher THC ratios and, in one case, a 200 mg high CBD dose:

Jadoon et al. (2016) demonstrated that treatment of 62 subjects with noninsulin-treated type 2 diabetes with 200 mg CBD per day or 10 mg THCV per day or 10 mg CBD and 10 mg THCV per day or 200 mg CBD and 10 mg THCV per day were all well tolerated.

Palmieri et al. (2017) showed that 12 females with severe somatoform and dysautonomic syndrome following HPV vaccination were given up to a maximum dose of 150 mg/ml CBD per day. This dose was well tolerated.

Paolicelli et al. (2015) found that MS patient receiving an average of 6.5±1.6 of Sativex sprays each day (16.25 mg of CBD/day and 16.25 mg of THC) had no serious adverse effects.

Hoggart et al. (2015) showed that patients with peripheral neuropathic pain (PNP) received on average 21.6 mg of THC and 20 mg of CBD per day and this dose was well tolerated.

Serpell et al. (2014) found that patients with peripheral neuropathic pain (PNP) received 24.03 mg of THC and 22.5 mg of CBD (8.9 spray of Sativex on average) and the spray was well tolerated.

Zuardi et al. (2009) treated Parkinson's disease with CBD (started with an oral dose of 150 mg/day) for 4 weeks and found no adverse effect during the treatment.

Brady et al. (2004) showed that average dose of THC/CBD of 33.7 mg each in MS patients with advanced MS and refractory lower urinary tract symptoms (LUTS) was well tolerated.

Collin et al. (2007) used on average 25.38 mg of THC and 23.5 mg of CBD (9.4 sprays of Sativex) to treat MS and found it well tolerated.

In one embodiment of the proposed invention, the treatment of a patient with an autoimmune disease Rheumatoid arthritis involves giving to a patient every 12 hours by oral administration a one ARCO® Chemie 60 Oval soft-gel capsule of the compound containing a mixture of 5 mg delta-9 and delta-8-tetrahydrocannabinol (THC) and cannabidiol (CBD) in the ratio of approximately 0.7 (THC) and 2 (CBD) by mass, and such mixture contains less than 5 mg of other cannabinoids co-extracted with THC and CBD from the *Cannabis* indica plant and not completely removed from the extract, and in one embodiment, one or more non-cannabinoid components, such as sesame oil and a mixture of parahydroxybenzoates, where such capsule is a time-released capsule designed to release said compound in the small intestine; and in another embodiment, in the stomach. The aforesaid compound and method have statistically meaningfully reduced perception of pain on the Rheumatoid Arthritis Pain Scale (RAPS) in subjects suffering from pain associated with Rheumatoid Arthritis inflammation after being administered for 5 days, having minimal to nonexistent debilitating psychotropic effect. RAPS measures physiological, sensory-discriminative, and cognitive components.

In another embodiment of the proposed invention, the treatment of ALS involves giving to a patient before bed time by oral administration a dose of medicament—in one embodiment, one extended release ARCO® Chemie 60 Oval soft-gel capsule and one immediate release ARCO® Chemie 60 Oval soft-gel capsule of the compound containing in each capsule a 40 mg mixture of delta-9-tetrahydrocannabinol (THC) and the cannabidiol (CBD) in the ratio of approximately 1.5 (THC) and 2 (CBD) by mass, and such mixture contains up to 5% Tetrahydrocannabinolic Acid (THCA) that remained in the extract after its decarboxylation, and in one embodiment, one or more non-cannabinoid components, such as medium chain triglycerides-containing palm kernel oil. This method provides effective control of spasms, muscle cramps and fasciculation symptoms at bed time with a desired mild psychotropic effect acting as a sleeping aid.

In another embodiment of the proposed invention, the treatment of MS involves giving to a patient two times a day by oral administration a dose of medicament, in one embodiment, a soft-gelatin capsule that consists of type A and/or B gelatin, water, and a plasticizer, such as glycerin or sorbitol; and encapsulates a compound containing a liquid mixture that includes: 10 mg of delta-9-tetrahydrocannabinol (THC), 20 mg of cannabidiol (CBD), sesame oil, methyl and propyl parabens, trace amount of other cannabinoids, and trace amount of other substances.

The proposed invention provides methods and compounds for treatment of multiple diseases and disorders at various stages, and different patients potentially presenting different symptoms, and as such may require larger or smaller doses to achieve the desired efficacy. Besides, certain variations of THC/CBD ratios and other components may be required to achieve the desired effect, such as the night or day-time application.

In one aspect of the invention, titration of doses is beneficial to patients as they can take smaller doses of the medication to achieve efficacy. It is understandable that not all patients will require the same dose of medication, for example patients of a larger build or faster metabolism may require a higher dose than that required by a patient that is of a smaller build or slower metabolism. In one embodiment said titration is adjusted with a time-release and point of release-tailored dosage forms. For instance, a soft-gelatin capsule designed to release medication in doses in certain parts of the digestive system to achieve the desired efficacy.

In another embodiment, the dose of medicament to be administered to a subject suffering from MS-related spasticity is formulated such that a specific patient can titrate such dose; where the term "titrate" means that the patient is provided with a medication that is in such a form or engineered in such a way that smaller doses than the unit dose can be taken. In one embodiment, the titratable dosage forms are gel, gel spray, transdermal patch, liquid, vapor, and the like.

The unit dosage-defined as a maximum dose of medication that can be taken at any one time or within a specified dosage period—may range, in one embodiment, between 20 and 40 mg of said medicine, or, depending on the administration route and aforesaid variables, the dosage may fluctuate significantly, such that unit dosage may consist of multiple doses taken several times a day. Administration of the compound may be carried out by any of several suitable known means, including but not limited to intraperitoneal, subcutaneous, oral, intramuscular, intravenous, etc.

These and other embodiments and objects of the invention will become apparent upon further review of the specification and claims presented herein. Thus, the above and the following expressed embodiments and objects of the invention are not intended by the inventors to limit the scope of the invention.

BRIEF DESCRIPTION OF THE DRAWINGS

The accompanying drawings, which are incorporated in and constitute a part of this specification, illustrate aspects of the present teachings and together with the description, serve to explain principles of the present teachings.

The FIG. 1, incorporated herein by reference, compares the oxidation potentials of cannabinoids and the antioxidant butylated hydroxytoluene (BHT). The oxidation profiles of (750 μM) BHT, cannabinoids, and anandamide were compared by cyclic voltametry.

Anandamide, a cannabinoid receptor ligand with a noncannabinoid structure, was used as a nonresponsive control. Experiments were repeated three times with essentially the same results. (Hampson, Grimaldi, Axelrod, & Wink, 1998)

The FIG. 2, incorporated herein by reference, compares the oxidation potentials of cannabinoids and the antioxidant butylated hydroxytoluene (BHT). Effect of cannabidiol and THC on dihydrorhodamine oxidation. Cannabinoids were compared with BHT for their ability to prevent tert-butyl hydroperoxide-induced oxidation of dihydrorhodamine. Data represent mean values±SEM from a single experiment with three replicates. This experiment was repeated four times with essentially the same results. (Hampson, Grimaldi, Axelrod, & Wink, 1998)

The FIG. 3, incorporated herein by reference, shows changes in Ashworth scores of MS patients from baseline to 13 weeks' follow-up, adjusted for ambulatory status and center effects. Mean (SD) changes in total Ashworth scores (baseline minus follow-up) were 1.24 (6.60), 1.86 (7.95), and 0.92 (6.56) for *cannabis* extract, delta-9-THC, and placebo, respectively. Corresponding figures for upper-body muscle groups were −0.05 (4.11), 0.48 (4.70), and −0.11 (4.04), and for lower-body muscle groups were 1.29 (4.37), 1.39 (5.21), and 1.04 (4.20). With both active treatments, an improvement over placebo was observed for the treatment effect when adjusted for center and for ambulatory status. (US Patent No. US20080175902 A1, 2007)

DESCRIPTION OF EMBODIMENTS

Reference will now be made to embodiments, examples of which are illustrated in the accompanying drawings. In the following description, some details are set forth in order to provide understanding of the proposed invention. However, it will be apparent to one of ordinary skill in the art that the present invention may be practiced without these details. In other instances, well-known methods, procedures, components, circuits, and networks have not been described in detail so as not to unnecessarily obscure aspects of the embodiments.

It will also be understood that, although the terms first, second, etc., may be used herein to describe various elements, these elements should not be limited by these terms. These terms are only used to distinguish one element from another. For example, a first contact could be termed a second contact, and, similarly, a second contact could be termed a first contact, without departing from the scope of the present invention. The first contact and the second contact are both contacts, but they are not the same contact.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. Moreover, the term "or" is intended to mean an inclusive "or" rather than an exclusive "or." That is, unless specified otherwise, or clear from the context, the phrase "X employs A or B" is intended to mean any of the natural inclusive permutations. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if is detected" may be construed to mean "upon determining" or "in response to determining" or "upon detecting (the stated condition or event)" or "in response to detecting (the stated condition or event)," depending on the context.

As used herein, the terms "related", "in connection", or "associated", or "relevant", and similar, depending on the context, means any association, whether direct or indirect, by any applicable criteria as the case may be.

The word "exemplary" is used herein to mean "serving as an example, instance, or illustration". And no aspect of this disclosure shall be construed as preferred or advantageous over other aspects or designs unless expressly stated.

Figure 3:
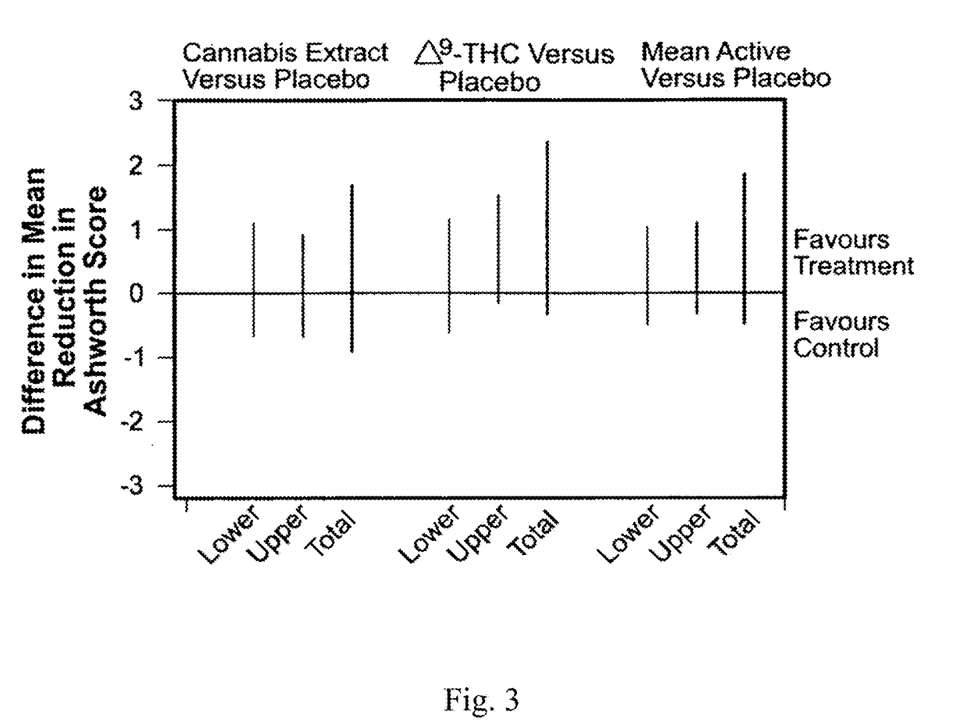

Cannabinoids are compounds usually derived from *Cannabis sativa*, an annual plant in the Cannabaceae family. The plant contains more than 420 different components, with 61 compounds of these belonging to the class of cannabinoids. The most active naturally occurring cannabinoids are tetrahydrocannabinol (THC) and cannabidiol (CBD), which are used for the treatment of a wide range of medical conditions, including neuropathic pain, spasticity associated with multiple sclerosis, fibromyalgia, and others. For instance, the FIG. 3, incorporated herein by reference, shows changes in Ashworth scores of MS patients from baseline to 13 weeks' follow-up, adjusted for ambulatory status and center effects. With both active treatments, an improvement over placebo was observed for the treatment effect when adjusted for center and for ambulatory status.

The present invention provides a treatment method of certain diseases and disorders, as well as a pharmaceutical compound that represents a stable, fast-acting formulation of naturally occurring cannabinoids or their analogs (for the purpose of this document, may be used interchangeably). An analog herein refers to a compound that is derived from a naturally occurring cannabinoid by chemical, biological or synthetic transformation of the naturally occurring cannabinoid. According to one aspect, therefore, are provided liquid compounds of cannabinoids in certain rations as disclosed herein.

Illustrative of cannabinoids or cannabinoid analogues are compounds selected from the group consisting of cannabinol, cannabidiol, $\Delta 9$-tetrahydrocannabinol, $\Delta 9$-tetrahydrocannabinol, 11-hydroxy-tetrahydrocannabinol, 11-hydroxy-$\Delta 9$-tetrahydrocannabinol, levonantradol, $\Delta 11$-tetrahydrocannabinol, tetranydrocannabinol, tetrahydrocannabivarin, dronabinol, amandamide, nabilone, a combination thereof, a natural or synthetic analogue thereof, and a natural or synthetic molecule with a basic cannabinoid structure.

The natural cannabinoid compounds are readily obtained from plant tissue by suspending the tissue in an appropriate solvent to extract cannabinoid compounds and other tissue components. Analytical purification of such an extract provides pharmaceutical grade cannabinoid compounds. Alternatively, cannabinoid compounds are extracted from plant tissue under supercritical conditions. Solvents used for supercritical extraction of cannabinoids include without limitation: carbon dioxide, or other gases in isolation or combination with or without solvent modifiers, selected from ethanol, propanol, butanol, hexane, chloroform, dichloromethane, acetone, or any organic solvent capable of extracting cannabinoids, and alcohol-water mixtures, for instance, water-ethanol or water-butanol mixtures, etc.

The present invention, in one embodiment, involves producing an extract from *cannabis* plant matter, containing tetrahydrocannabinol, cannabidiol and optionally the carboxylic acids thereof. In one embodiment, the dried plant matter is ground and subjected to a CO2 extraction and the primary extract obtained is separated. Specifically, ground *Cannabis* plant material is compressed and charged into an extraction vessel. CO2 is then introduced, having been brought to a temperature, in one embodiment, of approximately 60° C. and to a pressure of approximately 250 bars. When the CO2 enters into contact with the material to be extracted, it extracts the desired cannabinoid components, in particular comprising $\Delta 9$-tetrahydrocannabinol and cannabidiol, as well as the carboxylic acids thereof. In one embodiment, the extraction method permits extracting various isomers of tetrahydrocannabinol, selectively obtained from industrial hemp and from drug-producing hemp, also separating undesirable waxes and removing the solvent.

Cannabinoids, including THC, can be isolated from *Cannabis* plants using the CO2 extraction or any other extraction method, or can be made semi-synthetically as stated above. It is preferable, in one embodiment, that the extraction/production method yields substantially the $(-)-\Delta^9$-trans-THC isomer that is the most active isomer of THC. There are also various techniques that are known for isolating and separating the $(-)-\Delta^9$-trans-THC isomer from other compounds in THC. For example, U.S. Pat. No. 7,449,589 describes methods for purifying the $(-)-\Delta^9$-trans-THC isomer from a mixture of other THC isomers. (U.S. Pat. No. 7,449,589 B2, 2004)

However, THC, and in particular the $(-)-\Delta^9$-trans-THC isomer, is very unstable. Also, chemical synthesis and isolation of $(-)-\Delta^9$-trans-THC are both challenging. The $(-)-\Delta^9$-trans-THC isomer is very prone to acid-catalysed isomerization to the $\Delta^8$-THC isomer, is easily oxidized by oxygen to form inactive cannibinol, and is also sensitive to light and heat. All of these factors make it difficult to synthesize, purify, and store a high purity THC compound comprising the $(-)-\Delta^9$-trans-THC isomer which is stable over time and under various storage conditions.

In one embodiment, female *Cannabis* plant flowers of species 1, breed A are used for CO2 supercritical extraction of *cannabis* oil with prior grinding and decarboxylation via a forced air oven (above 100° C.), where the extract contains 22% THC/THCA and 6% CBD. And another female *Cannabis* plant of species 1, breed B, or in another embodiment, species 2, is used for CO2 supercritical extraction of *cannabis* oil with prior grinding and decarboxylation via forced air oven (above 100° C.), where the extract contains 0.2% THC/THCA and 18% CBD. In another embodiment, the extracts 1 and 2 are further purified to increase the content of THC and CBD using orthogonal flash column chromatography, distillation or other techniques, to obtain concentrations of THC and CBD isolates in the extracts, in one embodiment, of at least 55%. In another embodiment, the concentrated extracts 1 and 2 are dissolved in sufficient quantity of ethanol to increase their mobility, combined in desired proportions, and mechanically stirred, blending and at the temperature of at least 25° C. to obtain the desired ratio of THC and CBD in the produced mixture. In one embodiment, this ratio is 1-part of THC to 2-parts of CBD, and in another embodiment this ratio is 1-part of THC to 4-parts of CBD. The resulted compound can be further concentrated or, in one embodiment, purified by washing with ethanol (winterization), where ethanol is then removed by evaporation at low pressure to the amount, in one embodiment, of less than 50 mg PDE. In another embodiment, the resulted compound is heated to the temperature of at least 25° C. and mixed with Sesame Oil USP (CAS Number: 8008-74-0) in the ratio of 1:10, respectively. The resulted substance was then used to produce 300 mg hard gelatin capsules.

In another embodiment, an isomer mixture of chemically synthesized and at least 98% pure THC oil or crystals are dissolved in ethanol. The solution is then added in the desired proportions to the extract 2 (in place or in addition to the extract 1, see above), blended and further processed as described above. In another embodiment, a chemically synthesized 98% pure CBD is dissolved in ethanol. It is then added to the extract 1 (in place or in addition to the extract 2) and further processed as described above. In another embodiment, an isomer mixture of chemically synthesized THC is combined with chemically synthesized CBD in the desired proportions. They are then dissolved in a solvent and mechanically agitated until they are evenly dispersed in the resulted mixture. Ethanol is then removed by evaporation at low pressure to the quantity of less than 50 mg PDE. In one embodiment, the compound is then further purified by re-crystallization.

In one embodiment, a compound contains 68% mixture of 1-part THC and 2-parts of CBD and 32% of other phytochemicals, traces of elemental impurities and solvents. Said compound is blended at a temperature above 25° C. to increase mobility with palm oil and methyl propyl paraben mixture where the concentration of palm oil in the mixture is above 50%. The compound is then packaged into ARCO® Chemie 40 Oval gel capsules and bottled into a 100 cc HDPE plastic packer bottles (38-400), and in another embodiment packaged into blisters of 10 pills per blister.

In another embodiment, a compound containing at least 97% botanical concentrated resin, or in another embodiment, a crystallin mixture of 1-part THC and 1.5-parts of crystal CBD and 3% or less of impurities, such as traces of elemental impurities, solvents, and THC/CBD synthesis byproducts and/or degradation products. Said compound is dissolved in a solvent and blended with a powered modified silica oxide or another inert adsorbent excipient, as well as small quantities of other chemicals until the substances are evenly distributed. Where in one embodiment, the concentration of THC/CBD compound in the resulting mixture is above 5%. The remaining solvent in the compound is then evaporated to the quantity, in one embodiment, of less than 50 mg PDE. The resulted compound is then mechanically grinded to a fine powder adequate for pressed-tableting. The powder is then press-tableted into a standard convex oval 200 mg tablet, being coated prior to pressing with a lubricating coating, and after the tablet is pressed, coated with an enteric coating, then blister-packaged 10 pills per blister.

In another embodiment, a compound containing at least 38% oil mixture of 0.5-parts THC to 2-parts CBD, as well as 62% of other chemicals, elemental impurities and solvents is added into a melted coconut oil and beeswax, in one embodiment, in the proportion of 1:1:10. Polysorbate 20, in one embodiment, is added as a surfactant, as well as sodium gluconate as a stabilizer. The mixture is mechanically agitated at a temperature above 25° C. to increase mobility until the ingredients are evenly distributed. In one embodiment, lavender oil is added into the compound as an aroma additive. The topical compound produced is then bottled in plastic cream tubes.

It is not the purpose of present disclosure to provide particulars concerning the attainment of a colloidal formulation that is stable under a range of conditions. Though, in one embodiment, the disclosed compound to be used for gel-cap tableting with initial purity (HPLC) of THC and CBD being at least 98% by area can achieve stability such that at least 95% by area remains in undegraded form after exposure of the compound to the storage conditions for twelve months, where the ambient temperature is between 20° C. and 40° C. and relative humidity is between 55% and 75%.

In one embodiment, the stability of said compound is attained by contacting a solution containing cannabinoids into a solvent such as water, $C_1$-$C_6$ aliphatic alcohols, or mixtures of water and alcohols, acetone, or other water-miscible organic solvents that can be used to dissolve the cannabinoids; and in another embodiment, with addition of pharmaceutically acceptable buffers, stabilizers, and other pharmacologically inactive substances.

In one embodiment, the inventive cannabinoid compound is in the form of micelles or liposomes that encapsulate a cannabinoid within the membrane of the micelles or liposomes. Within the context of the present technology, the term "micelle" refers to an aggregate of surfactant molecules dispersed in a liquid colloid, while "liposome" refers to a vesicle composed of a mono or bilayer lipid.

In yet another embodiment, other drugs, and pharmaceutically acceptable carriers if present, may be in the lipophilic membrane or entrapped in the aqueous fluid that forms the core of the liposome. The entrapped cannabinoids contribute to the stability of the micelle/liposome membranes, such that the micelle/liposomes formulations may be used as an improved, fast, reliable and efficient system for the oral, enteral, parenteral, intravenous or topical delivery of cannabinoids and/or additional drugs to subjects in need thereof. The term "subject" or "patient" refers to a mammal in need of treatment or undergoing treatment using the inventive compounds described herein. Mammalian subjects include without limitation humans, dog, cat, horse or any other animal in need of treatment.

In another embodiment, unilamellar micelles or liposomes that are thermostable at temperatures greater than 50° C. are used in the manufacture of cannabinoid compound, according to the present invention. These micelles or liposomes are obtained by contacting a solution of a cannabinoid (a cannabinoid extract), with an aqueous solvent or an aqueous solution of a pharmaceutically active compound or drug. The mixing of the cannabinoid solution occurs in a manner suitable for the rapid dissolution of the cannabinoid solution in the aqueous solution. This can be accomplished through a variety of means including dilution, injection through a small orifice under pressure, and ultrasonic atomization.

And yet in another embodiment, the disclosed compound has advantageous properties, where the micellar and liposomal compound is stable at high temperatures, exceeding 50° C., is stable to sonication, capable of carrying large payloads of cannabinoids as well as other drugs suitable for use in combination therapy and can be stored for extended periods of time, for example greater than 20 weeks at 25° C.

In certain embodiments, said compound can be in the form of a concentrated, stable colloidal suspension that is obtained by infusing a solvent solution containing the cannabinoid extract or pure cannabinoids into a solvent such as water, with or without buffer. Stabilizing agent, for instance, a polymer or compounds selected from cellulose hyaluronic acid, polyvinyl pyrrolidone (PVP), alginate, chondritin sulfate, poly gamma glutamic acid, gelatin, chitisin, corn starch and flour can be used to stabilize the micelle formulations.

In one embodiment, said compound also exhibits superior systemic delivery and release of cannabinoids from the micelle or liposomes used in the manufacture of the inventive compound. The release of a cannabinoid from a liposome or micelle of the inventive compound can be modulated by changing the ratio of the concentration of lipid to the concentration of cannabinoid present in the liposome.

In one embodiment, tissue specific delivery can be achieved by modifying the surface of the liposomes or micelles with compounds that bind specifically to biological macromolecules expressed on cellular surfaces. For instance, the micelle or liposomal surface can be derivatized to display an antibody specific to an antigen expressed on cancer cells.

According to one embodiment, said compound that is used in the treatment of a disease condition is administered to a patient or subject in need of treatment either alone or in combination with other compounds/drugs having similar or different biological activities. For example, said compound may be administered in a combination therapy, i.e., either simultaneously in single or separate dosage forms or in separate dosage forms within hours or days of each other. Examples of compounds/drugs used in such combination therapies include without limitation: chemotherapeutic agents, immunosuppressive agents, immunostimulatory, anti-pyretic, cytokines, opioids, cytokines, cytotoxic agents, nucleolytic compounds, radioactive isotopes, receptors, prodrug activating enzymes, which may be naturally occurring or produced by recombinant methods, anti-inflammatory agents, antibiotics, protease inhibitors, growth factors, osteo-inductive factors and the like.

In some embodiments, the compound further contains, in accordance with accepted practices of pharmaceutical compounding, one or more pharmaceutically acceptable excipients, including without limitation: diluents, adjuvants, stabilizers, emulsifiers, preservatives, colorants, buffers, flavor imparting agents. As stated above, said compound may contain a cannabinoid, an analog of a cannabinoid, or both and may be consumed directly or formulated into nutraceutical or pharmaceutically acceptable compounds suitable for oral, enteral, parenteral, intravenous or topical administration.

The term "parenteral" as used herein includes subcutaneous injections, intravenous, intramuscular, intrasternal injection or infusion techniques. Such excipients are well known in the art. Dosage forms for oral administration include food, beverages, drinks, soups, baked goods, syrups, oral pharmaceutical compounds, nutraceutical formulations, and the like. Suitable pharmaceutical carriers include any such materials known in the art, e.g., any liquid, gel, solvent, liquid diluent, solubilizer, polymer or the like, which does not significantly interact with other components of the formulations in a deleterious manner.

Liquid dosage forms for oral administration include, but are not limited to, pharmaceutically acceptable emulsions, solutions, suspensions, syrups and elixirs. In addition to the cannabinoid extract, the liquid dosage forms can contain inert diluents commonly used in the art. For instance, liquid formulations can contain water, alcohol, polyethylene glycol ethers, and any other pharmaceutically acceptable solvents. Solubilizing agents and emulsifiers such as, without limitation: ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols, fatty acid esters of sorbitan and mixtures thereof may also be present in said compound.

Additionally, oral compound of the proposed invention can include, without limitation, adjuvants such as wetting agents, emulsifying and suspending agents, sweetening, flavoring, and perfuming agents. When formulated as a suspension, said compound may contain the cannabinoid extract and suspending agents, for example, without limitation: ethoxylated isostearyl alcohols, polyoxyethylene sorbitol, sorbitan esters, microcrystalline cellulose, aluminum metahydroxide, bentonite, agar-agar, tragacanth, and mixtures thereof.

In one embodiment, the emulsifier may comprise a mixture of monoglyceride and diglyceride at a total concentration of 1% to 99% w/w and a carrageenan or mixture of carrageenans at a total concentration of 0.01% to 10% w/w. In another embodiment, the emulsifier may be present in a concentration range of 1% to 99%, 5% to 80%, 10% to 35%, 10% to 20%, or about 15%-25%% w/w.

Solid dosage forms suitable for oral administration include, capsules, tablets, pills, powders, and granules. In such solid dosage forms, the cannabinoid extract can be used alone or in combination with one or more drugs that are mixed with at least one pharmaceutically acceptable excipient or carrier such as sodium citrate or dicalcium phosphate and/or fillers or extenders such as starches, lactose, sucrose, glucose, mannitol, and silicic acid; binders such as, for example, carboxymethylcellulose, alginates, gelatin, polyvinylpyrrolidone, sucrose, and acacia; humectants such as glycerol; disintegrating agents such as agar-agar, calcium carbonate, potato or tapioca starch, alginic acid, certain silicates, and sodium carbonate; solution retarding agents such as paraffin; absorption accelerators such as quaternary ammonium compounds; wetting agents such as, for example, acetyl alcohol and glycerol monostearate; absorbents such as kaolin and bentonite clay; and lubricants such as talc, calcium stearate, magnesium stearate, solid polyethylene glycols, sodium lauryl sulfate, and mixtures thereof. For capsules, tablets and pills, the dosage form can also comprise buffering agents.

Micellular or liposomal suspensions can be encapsulated with a variety of polymers, sugars, and chelating agents, to yield stable solid liposomal cannabinoid preparation. Encapsulation can take the form of cross-linked polymers, trapping of the micells or liposomes within a non-crosslinked polymer network, or dispersed within the crystalline structure of sugar starches or protein molecules. These granules can be further processed to yield sublingual films, suppositories, dispersible powder, tablets, gel capsules, etc.

Solid dosages in the form of tablets, capsules, pills, and granules can be coated using compounds that accelerate or decrease the release of cannabinoids. For instance, the proposed invention also encompasses solid dosage forms having enteric coatings, extended-release coatings, sustained-release coatings, delayed release coatings and immediate-release coatings. Methods used to coat solid dosage forms as well as the materials used to manufacture such coatings are well known in the pharmaceutical formulary art. The solid dosage forms can optionally contain opacity enhancing agents. According to an embodiment, the solid dosage form comprises an enteric coating that permits the release of a cannabinoid or cannabinoid analog alone or in combination with one or more drugs at a specific location within the gastrointestinal tract, optionally, in a delayed manner. Exemplary of such coating materials include glyceryl monostearate or glyceryl distearate may be employed, polymeric substances and waxes. The cannabinoid extract, for instance, a cannabinoid or cannabinoid analog alone or in combination with one or more drugs can also be in micro-encapsulated form, if appropriate, with one or more of the above-mentioned excipients.

In one embodiment, said compound is packaged into a gelatin capsule dosage form. In another embodiment, the compound is packaged into a non-gelatin capsule or an HPMC capsule. Said capsule can be a vegan based capsule or else. The compound disclosed herein includes a sustained release compound, an immediate release compound, or a combined sustained release fraction and immediate release fraction. In one embodiment, the therapeutic effect of the compound has a duration up to 10 hours, up to 11 hours, up to 12 hours, up to 14 hours, up to 16 hours, up to 18 hours, or up to 24 hours. In one embodiment, the compound disclosed herein comprises an immediate release (IR) fraction and a sustained release (SR) fraction, wherein the immediate release fraction comprises a therapeutically effective amount of cannabinoids and an edible oil; and wherein the sustained release fraction comprises a therapeutically effective amount of cannabinoids, and a mixture of emulsifiers and other pharmacologically inactive substances.

In another embodiment, a dietary compound, according to the present invention, is any ingestible preparation that contains the cannabinoid suspensions of the invention mixed with a food product. The food product can be dried, cooked, boiled, lyophilized or baked. Breads, teas, soups, cereals, salads, sandwiches, sprouts, vegetables, animal feed, pills and tablets, are among the vast number of different food products contemplated in the present invention.

In yet another embodiment, a compound for parenteral injection comprises pharmaceutically acceptable sterile aqueous or non-aqueous solutions, dispersions, suspensions or emulsions as well as sterile powders for reconstitution into sterile injectable solutions or dispersions prior to use. Examples of suitable aqueous and non-aqueous carriers, diluents, solvents or vehicles include, without limitation, water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate.

In one embodiment, proper fluidity can be maintained, for example, by the use of coating materials such as lecithin, by the maintenance of the required particle size in the case of dispersions, and by the use of surfactants. The compound of the present invention can also contain adjuvants such as, but not limited to, preservatives, wetting agents, emulsifying agents, and dispersing agents. The compound for parenteral delivery generally includes isotonic agents such as sugars, sodium chloride, and the like. Prolonged absorption of the injectable pharmaceutical formulation can be brought about by the inclusion of agents which delay absorption such as aluminum monostearate and gelatin.

Injectable depot forms are made by forming microencapsule matrices of the drug in biodegradable polymers such as polylactide-polyglycolide. Depending upon the ratio of drug to polymer and the nature of the specific polymer employed, the rate of drug release can be controlled. Examples of other biodegradable polymers include poly-orthoesters and polyanhydrides. Depot injectable formulations are also prepared by entrapping the drug in liposomes or microemulsions which are compatible with body tissues. The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Dosage forms for topical administration include, but are not limited to, ointments, creams, emulsions, lotions, gels, sunscreens and agents that favor penetration within the epidermis. Various additives, known to those skilled in the art, may be included in the topical formulations of the invention. Examples of additives include, but are not limited to, solubilizers, skin permeation enhancers, preservatives (e.g., anti-oxidants), moisturizers, gelling agents, buffering agents, surfactants, emulsifiers, emollients, thickening agents, stabilizers, humectants, dispersing agents and pharmaceutical carriers. Examples of moisturizers include jojoba oil and evening primrose oil.

Suitable skin permeation enhancers are well known in the art and include lower alkanols, such as methanol ethanol and 2-propanol; alkyl methyl sulfoxides such as dimethylsulfoxide (DMSO), decylmethylsulfoxide (C10 MSO) and tetradecylmethyl sulfoxide; pyrrolidones, urea; N,N-diethyl-m-toluamide; C2-C6 alkanediols; dimethyl formamide (DMF), N,N-dimethylacetamide (DMA) and tetrahydrofurfuryl alcohol. Examples of solubilizers include, but are not limited to, hydrophilic ethers such as diethylene glycol monoethyl ether (ethoxydiglycol, available commercially as Transcutol) and diethylene glycol monoethyl ether oleate (available commercially as Softcutol); polyoxy 35 castor oil, polyoxy 40 hydrogenated castor oil, polyethylene glycol (PEG), particularly low molecular weight PEGs, such as PEG 300 and PEG 400, and polyethylene glycol derivatives such as PEG-8 caprylic/capric glycerides (available commercially as Labrasol); alkyl methyl sulfoxides, such as DMSO; pyrrolidones, DMA, and mixtures thereof.

Prevention and/or treatment of infections can be achieved by the inclusion of antibiotics, as well as various antibacterial and antifungal agents, for example, paraben, chlorobutanol, phenol sorbic acid, and the like, in the compounds of the invention.

One of ordinary skill will appreciate that effective amounts of the agents in the compound used in the methods of the invention can be determined empirically. It will be understood that, when administered to a human patient, the total daily usage of the compound of the present invention will be decided by the attending physician within the scope of sound medical judgment. The specific therapeutically effective dose level for any patient will depend upon a variety of factors: the type and degree of the response to be achieved; the activity of the specific compound employed; the age, body weight, general health, sex and diet of the patient; the duration of the treatment; drugs used in combination or coincidental with the method of the invention; and like factors well known in the medical arts.

The formulations of the invention, in one embodiment, are therefore particularly suitable for oral administration and may be administered to subjects with a pre-existing condition or pre-disposed to certain disease conditions, such as without limitations: autoimmune diseases and disorders, motor neuron diseases and disorders, neurodegenerative diseases and disorders, pain associated with cancer and trauma; and other conditions, as contemplated by the invention, that include, but are not limited to: gastrointestinal, metabolic, neurological, circulatory, soft tissue, musculoskeletal, chronic or acute pain, nausea, decreased appetite, skin disorders, sexual dysfunction, glaucoma, AIDS wasting, neuropathic pain, treatment of spasticity associated with MS, SCI, HSP, SDCP, and SA, fibromyalgia, chemotherapy-induced nausea, allergies, inflammation, infection, epilepsy, depression, migraine, bipolar disorders, anxiety disorder, dependency and withdrawal. In addition, the methods of the invention may be used to alleviate, or relief relieve symptoms or side effects associated with anti-retroviral therapy, chemotherapy and radiation therapy.

In one embodiment of the proposed invention, the treatment of chorea symptoms in a patient suffering from a late stage Huntington's motor neuron disease involves giving to a patient one 300 mg oral capsule every 8 hours of the compound containing 20 mg THC and 60 mg CBD, and such mixture contains a small amount of other cannabinoids, and in one embodiment, one or more non-cannabinoid components, such as sesame oil, where such capsule is a time-released capsule designed to release said mixture in the small intestine; and in another embodiment, in the stomach. A higher THC dose, in this case, is required since patients with late stage HD loose CB1 receptors.

In another embodiment of the proposed invention, the treatment of cancer pain involves giving to a patient who is undergoing a radiation treatment an intravenous dose of 3 mg every 6 hours of medicament, in one embodiment, where the patient also receives 5 mg of morphine sulfate intravenously every 6 hours, and where said medicament contains a mixture of THC and CBD in the ratio of approximately 1.8 (THC) and 1.5 (CBD) by weight, and such mixture contains a small amount of other cannabinoids, and in one embodiment, one or more non-cannabinoid components, such as Refined Sesame Oil injectable grade as a solubilizer. This method provides effective control of pain, delaying the escalation of highly addictive morphine due to the buildup antinociceptive tolerance.

In one embodiment of the proposed invention, the treatment of arthritis inflammation involves applying every 6 hours a topical cream solution that contains at least 38% mixture of 0.5-parts THC to 2-parts CBD combined with coconut oil, beeswax, polysorbate, and sodium gluconate. The aforesaid compound is absorbed through the patient's skin. After being administered for 30 days, a marked reduction of swelling and redness is produced. Also, the pain associated with arthritis is reported to decrease in 2 hours after the first administration, being progressively decreasing over the period of 30 days.

In another embodiment of the proposed invention, there is a patient affected by primary progressive MS, according to McDonald 2001 criteria, and treated with beta-interferon (INF-$\beta$). The patient presented a moderate to severe spasticity partially responsive to baclofen 50 mg/daily. The patient experienced a clinical relapse characterized by ataxia with an Expanded Disability Scale of 6, a Modified Ashwort Scale (MAS) of 3+, Numeric Rating Scale for Spasticity (NRS) of 10, and Ambulation Index (AI) of 5. The treatment of primary progressive MS involves giving to a patient two times a day by oral administration a dose of medicament, in one embodiment, 200 mg oval soft-gelatin capsule that consists of type A and/or B gelatin, water, and a plasticizer, such as glycerin or sorbitol; and encapsulates a compound containing a liquid mixture that includes: 10 mg of THC, 20 mg of CBD, natural oil, methyl and propyl parabens, small amount of other cannabinoids, and other substances. At one month-follow-up the subject had a good response to the treatment, as showed by nearly all the clinical scales (MAS 3-, NRS 6, AI 5). Said medicament is proposed to be used before baclofen therapy as a second-line treatment for patients taking other anti-spasticity medications (e.g. oral agents such as baclofen, benzodiazepine, and others) or monotherapy for patients who are intolerant to anti-spasticity medications.

In support of the cannabinoid treatment effectiveness for MS spasticity, in a double-blind, crossover, dose-escalation study, 57 MS patients were randomized to two groups, A and B. The subjects were either treated with *cannabis* extract (each capsule containing 2.5 mg THC and 0.9 mg CBD) in an escalation phase of 15 mg to a maximum of 30 mg THC (increasing by 5 mg) for 14 days before starting placebo treatment for 7 days or vice-versa. Daily self-reports of spasm frequency and symptoms were measured using the following: Ashworth Scale, Rivermead Mobility Index, 10-m timed walk, nine-hole peg test, paced auditory serial addition test, and the digit span test. In 37 patients who received at least 90% of the prescribed dose, active treatment was associated with a greater improvement of the secondary outcome of spasm frequency (p=0.013) in addition to improvements in mobility (p=0.01). However, neurobehavioral side effects emerge, especially in predisposed individuals due to the THC psychotropic activity. Increased amount of CBD, double the amount of THC, as proposed in this invention, reduces the neurobehavioral side effects via the suggested pharmacological mechanism.

It further should be noted that there are existing pharmaceuticals for other indications that separately contain THC and CBD but not a combination drug in the ratios proposed by this invention. Limited clinical trials demonstrate positive effects on the symptoms contemplated herein (Table 1). However, they produce side effects that limit their utility. A cannabinoid dose-related psychotropic effect has been reported by patients receiving Marinol (synthetic THC) in both the antiemetic (24%) and the lower dose appetite stimulant clinical trials (8%) (AbbVie Inc., 2017). The most frequently reported adverse experiences in patients with AIDS during placebo-controlled clinical trials involved the CNS and were reported by 33% of patients receiving Marinol (AbbVie Inc., 2017). About 25% of patients reported a CNS adverse reaction during the first 2 weeks and about 4% reported such a reaction each week for the next 6 weeks thereafter (AbbVie Inc., 2017).

The proposed new formulations are essentially free of said shortcomings due to the augmented pharmacology of the actives when used in certain combinations as disclosed herein.

TABLE 1

Overview of controlled trials of cannabis medications for spasticity.

| Indication | Number of randomized controlled trials (some three-armed) | Positive results | Negative results |
|---|---|---|---|
| Spasticity | n = 12 (dronabinol: [e1, e2, e4-e6]; cannabis: [e1-e3, e6-e12]) in MS<br>n = 3 (dronabinol: [e13-e14]; nabilone: [e15] in paraplegia) | n = 9 (e4-e12)<br>n = 3 (e13-e15) | n = 3 (e1-e3)<br>— |
| Neuropathic pain | n = 14 (dronabinol: [e71-e74]; nabilone: [e75, e76]; cannabis extract: [e73, e74, e77-e79]; cannabis cigarettes: [e80-e83]; CT3 (ajulemic acid[1]): [e84]) in neuropathic pain or pain in MS | n = 12 (e71, e73-e75, e77-e84) | n = 2 (e72, e76) |

[e1: (Killestein, Hoogervorst, Reif, & et al., 2002); e2: (Zajicek, Fox, Sanders, & et al., 2003); e3: (Centonze, Mori, Koch, & et al., 2009); e4: (Petro & Ellenberger, Treatment of human spasticity with delta 9-tetrahydrocannabinol., 1981); e5: (Ungerleider, Andyrsiak, Fairbanks, Ellison, & Myers, Delta-9-THC in the treatment of spasticity associated with multiple sclerosis., 1987); e6: (Zajicek, Sanders, Wright, & et al., 2005); e7: (Vaney, Heinzel-Gutenbrunner, Jobin, & et al., 2004); e8: (Wade D. T., Makela, Robson, & et al., 2004); e9: (Wade D. T., Makela, House, & et al., 2006); e10: (Collin, Davies, Mutiboko, & Ratcliffe, 2007); e11: (Conte, Bettolo, Onesti, & et al., 2009); e12: (Novotna, Mares, Ratcliffe, & et al., 2011); e13: (Hanigan, Destree, & Truong, 1986) (abstract only); e14: (Hagenbach, Luz, Ghafoor, & et al., 2007); e15: (Pooyania, Ethans, Szturm, & et al., 2010); e71: (Svendsen, Jensen, & Bach, 2004); e72: (Rintala, Fiess, Tan, & et al., 2010); e73: (Wade, Robson, House, & et al., 2003); e74: (Berman, Symonds, & Birch, 2004); e75: (Wissel, Haydn, Müller, & et al., 2006); e76: (Frank, Serpell, Hughes, & et al., 2008); e77: (Rog, Nurmikko, Friede, & Young, 2005); e78: (Nurmikko, Serpell, Hoggart, & et al., 2007); e79: (Selvarajah, Gandhi, Emery, & Tesfaye, 2010); e80: (Abrams, Jay, Shade, & et al., 2007); e81: (Wilsey, Marcotte, Tsodikov, & et al., 2008); e82: (Ellis, Toperoff, Vaida, & et al., 2009); e83: (Ware, Wang, Shapiro, & et al., 2010); e84: (Karst, Salim, Burstein, & et al., 2003);
[1]Synthetic non-psychoactive cannobinoid derivative of the THC metabolite 11-nor-9-carboxy-THC.

The potential commercial uses of the disclosed preparations include, for example, protective/prophylactic and medical uses. The compounds of the invention can also be administered by a variety of other routes, including mucosal, subcutaneous and intramuscular administration, and may comprise a variety of carriers or excipients known in the formulary art, such as, non-toxic solid, semisolid or liquid filler, diluent, encapsulating material and formulation auxiliaries that are pharmaceutically acceptable.

The features disclosed in the foregoing description, or the following claims, or the accompanying drawings, expressed in their specific forms or in terms of a means for performing the disclosed function, or a method or system for attaining the disclosed result, as appropriate, may separately, or in any combination of such features, be utilized for realizing the invention in diverse forms While various embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments but should be defined in accordance with the following claims and their equivalents.

REFERENCES

AbbVie Inc. (2017). Merinol highlights of prescribing information. AbbVie Inc. Retrieved from https://www.accessdata.fda.gov/drugsatfda_docs/label/2017/018651s0291b1.pdf Abood, M. (2003). US Patent No. US20040018151 A1.

Abrams, D. I., Jay, C. A., Shade, S. B., & et al. (2007, Feb. 13). Cannabis in painful HIV-associated sensory neuropathy: a randomized placebo-controlled trial. Neurology, 68(7), pp. 515-21. doi:10.1212/01.wnl.0000253187.66183.9c Bayer HealthCare press release and Medical Update Memo of Multiple Sclerosis Society of Canada. (2005). Sativex—Novel cannabis derived treatment for MS pain now available in Canada by prescription. Toronto: Bio-based News. Retrieved from http://news.bio-based.eu/sativex-novel-cannabis-derived-treatment-for-ms-pain-now-available-in-canada-by-prescription Berman, J. S., Symonds, C., & Birch, R. (2004, December). Efficacy of two cannabis based medicinal extracts for relief of central neuropathic pain from brachial plexus avulsion: results of a randomised controlled trial. Pain, 112(3), pp. 299-306. doi:10.1016/j.pain.2004.09.013

Brady, C. M., DasGupta, R., Dalton, C., Wiseman, O. J., Berkley, K. J., & Fowler, C. J. (2004, August). An open-label pilot study of cannabis-based extracts for bladder dysfunction in advanced multiple sclerosis. Mult Scler., 10(4), pp. 425-33. doi:10.1191/1352458504ms1063oa Centonze, D., Mori, F., Koch, G., & et al. (2009, December). Lack of effect of cannabis-based treatment on clinical and laboratory measures in multiple sclerosis. Neurol Sci., 30(6), pp. 531-4. doi:10.1007/s10072-009-0136-5

Collin, C., Davies, P., Mutiboko, I. K., & Ratcliffe, S. (2007, March). Randomized controlled trial of cannabis-based medicine in spasticity caused by multiple sclerosis. Eur J Neurol., 14(3), pp. 290-6. doi:10.1111/j.1468-1331.2006.01639.x Conte, A., Bettolo, C. M., Onesti, E., & et al. (2009, May). Cannabinoid-induced effects on the nociceptive system: a neurophysiological study in patients with secondary progressive multiple sclerosis. Eur J Pain., 13(5), pp. 472-7. doi:10.1016/j.ejpain.2008.05.014

Dudley, R. (2005). US Patent No. US20060167084 A1.

Ellis, R. J., Toperoff, W., Vaida, F., & et al. (2009, February). Smoked medicinal cannabis for neuropathic pain in HIV: a randomized, crossover clinical trial. Neuropsychopharmacology, 34(3), pp. 672-80. doi: 10.1038/npp.2008.120

Formukong, E. A., Evans, A. T., & Evans, F. J. (1988, August). Analgesic and antiinflammatory activity of constituents of Cannabis sativa L. PubMed, 12(4), 361-371.

Frank, B., Serpell, M. G., Hughes, J., & et al. (2008, Jan. 26). Comparison of analgesic effects and patient tolerability of nabilone and dihydrocodeine for chronic neuropathic pain: randomised, crossover, double blind study. BMJ, 336(7637), pp. 199-201. doi:10.1136/bmj.39429.619653.80

Geiser, F. O., Keenan, J. J., & Ros, R. (2004). U.S. Pat. No. 7,449,589 B2.

Geiser, F., Keenan, J., Rossi, R., Sanchez, A., & Whelan, J. (2004). U.S. Pat. No. 7,449,589 B2.

Guy, G., & Platt, B. (2014). U.S. Pat. No. 9,205,063 B2.

Guy, G., & Robson, P. (2005). U.S. Pat. No. 7,968,594 B2.

GW Pharma Ltd. (n.d.). Sativex Oromucosal Spray. Retrieved from EMC: https://www.medicines.org.uk/emc/product/602/smpc Hagenbach, U., Luz, S., Ghafoor, N., & et al. (2007, August). The treatment of spasticity with Delta9-tetrahydrocannabinol in persons with spinal cord injury. Spinal Cord., 45(8), pp. 551-62. doi:10.1038/sj.sc.3101982

Hampson, A. J., Grimaldi, M., Lolic, M., Wink, D., Rosenthal, R., & Axelrod, J. (2000). Neuroprotective antioxidants from marijuana. *PubMed*, 274-282.

Hampson, A. J., Grimaldi, M., Axelrod, J., & Wink, D. (1998, Jul. 7). Cannabidiol and (−)Δ9-tetrahydrocannabinol are neuroprotective antioxidants. *Medical Sciences*, 95(14), pp. 8268-8273.

Hanigan, W. C., Destree, R., & Truong, X. T. (1986). The effect of D9-THC on human spasticity. *Clin Pharmacol Ther.*, 39, p. 198. Retrieved from https://www.cannabis-med.org/studies/ww_en_db_study_show.php?s_id=154

Hoggart, B., Ratcliffe, S., Ehler, E., Simpson, K. H., Hovorka, J., Lejčko, J., . . . Serpell, M. (2015, January). A multicentre, open-label, follow-on study to assess the long-term maintenance of effect, tolerance and safety of THC/CBD oromucosal spray in the management of neuropathic pain. *J Neurol*, 262(1), pp. 27-40. doi:10.1007/s00415-014-7502-9

Iuvone, T., Di Marzo, V., Guy, G., Wright, S., & Stott, C. (2012). US Patent No. US20140228438 A1.

Jadoon, K. A., Ratcliffe, S. H., Barrett, D. A., Thomas, E. L., Stott, C., Bell, J. D., . . . Tan, G. D. (2016, October). Efficacy and Safety of Cannabidiol and Tetrahydrocannabivarin on Glycemic and Lipid Parameters in Patients With Type 2 Diabetes: A Randomized, Double-Blind, Placebo-Controlled, Parallel Group Pilot Study. *Diabetes Care*, 39(10), pp. 1777-86. doi:10.2337/dc16-0650

Jamontt, J. M., Molleman, A., Pertwee, R. G., & Parsons, M. E. (2010, June). The effects of Δ9-tetrahydrocannabinol and cannabidiol alone and in combination on damage, inflammation and in vitro motility disturbances in rat colitis. *Br J Pharmacol*, 160(3), pp. 712-723. doi:10.1111/j.1476-5381.2010.00791.x Johnson, J. R., Lossignol, D., Burnell-Nugent, M., & Fallon, M. T. (2013, August). An open-label extension study to investigate the long-term safety and tolerability of THC/CBD oromucosal spray and oromucosal THC spray in patients with terminal cancer-related pain refractory to strong opioid analgesics. *J Pain Symptom Manage.*, 46(2), pp. 207-18. doi: 10.1016/j.jpainsymman.2012.07.014

Karniol, I. G., Shirakawa, I., Kasinski, N., Pfeferman, A., & Carlini, E. A. (1974, September). Cannabidiol interferes with the effects of Δ9-tetrahydrocannabinol in man. *European Journal of Pharmacology*, 28(1), pp. 172-177. doi: 10.1016/0014-2999(74) 90129-0

Karst, M., Salim, K., Burstein, S., & et al. (2003, Oct. 1). Analgesic effect of the synthetic cannabinoid CT-3 on chronic neuropathic pain: a randomized controlled trial. *JAMA*, 290(13), pp. 1757-62. doi:10.1001/jama.290.13.1757

Killestein, J., Hoogervorst, E. L., Reif, M., & et al. (2002, May 14). Safety, tolerability, and efficacy of orally administered cannabinoids in MS. *Neurology*, 58(9), pp. 1404-7. doi: 10.1212/WNL. 58.9.1404

Kluger, B., Triolo, P., Jones, W., & Jankovic, J. (2015, March). The Therapeutic Potential of Cannabinoids for Movement Disorders. *Mov Disord.*, 30(3), pp. 313-327. doi: 10.1002/mds.26142

Koppel, B. S., Brust, J. C., Fife, T., Bronstein, J., Youssof, S., Gronseth, G., & Gloss, D. (2014, Apr. 29). Systematic review: efficacy and safety of medical marijuana in selected neurologic disorders: report of the Guideline Development Subcommittee of the American Academy of Neurology. *Neurology*, 82(17), pp. 1556-63. doi: 10.1212/WNL.0000000000000363

Kottayil, G., Zhu, Z., & Gosko, V. R. (2005). US Patent No. U.S. Pat. No. 8,628,796B2.

Laprairie, R. B., Bagher, A. M., & Denovan-Wright, E. M. (2015, October). Cannabidiol is a negative allosteric modulator of the cannabinoid CB1 receptor. *Br J Pharmacol.*, 172(20), pp. 4790-805. doi:10.1111/bph.13250

Leussink, V. I., Husseini, L., Warnke, C., Broussalis, E., Hartung, H.-P., & Kieseier, B. C. (2012, September). Symptomatic therapy in multiple sclerosis: the role of cannabinoids in treating spasticity. *Ther Adv Neurol Disord.*, 5(5), pp. 255-266. doi: 10.1177/1756285612453972

Malfitano, A. M., Proto, M. C., & Bifulco, M. (2008, October). Cannabinoids in the management of spasticity associated with multiple sclerosis. *Neuropsychiatr Dis Treat.*, 4(5), pp. 847-853. Retrieved from https://www.ncbi.nlm.nih.gov/pmc/articles/PMC2626929/

Novotna, A., Mares, J., Ratcliffe, S., & et al. (2011, September). A randomized, double-blind, placebo-controlled, parallel-group, enriched-design study of Nabiximols® (Sativex®)), as add-on therapy, in subjects with refractory spasticity caused by multiple sclerosis. *Eur J Neurol.*, 18(9), pp. 1122-31. doi:10.1111/j.1468-1331.2010.03328.x Nurmikko, T. J., Serpell, M. G., Hoggart, B., & et al. (2007, Dec. 15). Sativex successfully treats neuropathic pain characterised by allodynia: a randomised, double-blind, placebo-controlled clinical trial. *Pain*, 133(1-3), pp. 210-20. doi:10.1016/j.pain.2007.08.028

Palmieri, B., Laurino, C., & Vadala, M. (2017, February). Short-Term Efficacy of CBD-Enriched Hemp Oil in Girls with Dysautonomic Syndrome after Human Papillomavirus Vaccination. *Isr Med Assoc J.*, 19(2), pp. 79-84. Retrieved from https://www.ncbi.nlm.nih.gov/pubmed/28457055

Paolicelli, D., Direnzo, V., Manni, A., D'Onghia, M., Tortorella, C., & Zoccolella, S. (2015, Nov. 26). Long-Term Data of Efficacy, Safety, and Tolerability in a Real-Life Setting of THC/CBD Oromucosal Spray-Treated Multiple Sclerosis Patients. *The Journal of Clinical Pharmacology*, 56(7), pp. 845-851. doi:doi.org/10.1002/jcph.670

Pertwee, R. G. (2008, January). The diverse CB1 and CB2 receptor pharmacology of three plant cannabinoids: Δ9-tetrahydrocannabinol, cannabidiol and Δ9-tetrahydrocannabivarin. *British Pharmacological Society*, 153(2), pp. 199-215. doi: 10.1038/sj.bjp.0707617

Petro, D. J., & Ellenberger, C. J. (1981, August-September). Treatment of human spasticity with delta 9-tetrahydrocannabinol. *J Clin Pharmacol.*, 21(8-9 Suppl), pp. 413 S-416S. Retrieved from https://www.ncbi.nlm.nih.gov/pubmed/6271839/

Petro, D. J., & Ellenberger, C. J. (1981, August-September). Treatment of human spasticity with delta 9-tetrahydrocannabinol. *J Clin Pharmacol.*, 21(8-9 Suppl), pp. 413 S-416S. doi: 10.1002/j.1552-4604.1981.tb02621.x Pooyania, S., Ethans, K., Szturm, T., & et al. (2010, May). A randomized, double-blinded, crossover pilot study assessing the effect of nabilone on spasticity in persons with spinal cord injury. *Arch Phys Med Rehabil.*, 91(5), pp. 703-7. doi: 10.1016/j.apmr.2009.12.025

Pryce, G., & Baker, D. (2007, February). Control of spasticity in a multiple sclerosis model is mediated by CB1, not CB2, cannabinoid receptors. *Br J Pharmacol.*, 150(4), pp. 519-25. doi: 10.1038/sj.bjp.0707003

Rintala, D. H., Fiess, R. N., Tan, G., & et al. (2010, October). Effect of dronabinol on central neuropathic pain after spinal cord injury: a pilot study. *Am J Phys Med Rehabil.*, 89(10), pp. 840-8. doi:10.1097/PHM.0b013e3181f1c4ec Rog, D. J., Nurmikko, T. J., Friede, T., & Young, C. A. (2005, Sep. 27). Randomized, controlled trial of *cannabis*-based medicine in central pain in multiple sclerosis. *Neurology.*, 65(6), pp. 812-9. doi:10.1212/01.wn1.0000176753.45410.8b Rossi, R., Silverberg, L., Hoga, R., & Shah, R. M. (2011). U.S. Pat. No. 8,980,940 B2.

Rudroff, T., & Honce, J. M. (2017, Jun. 23). *Cannabis* and Multiple Sclerosis—The Way Forward. *Front Neurol.*, p. 299. doi:10.3389/fneur.2017.00299

Russo, E., & Guy, G. W. (2006, Oct. 4). A tale of two cannabinoids: the therapeutic rationale for combining tetrahydrocannabinol and cannabidiol. *Med Hypotheses*, 66(2), pp. 234-46. Retrieved from https://www.ncbi.nlm.nih.gov/pubmed/16209908

Russo, M., Rifi, C., Sessa, E., & et al. (2015). Sativex-induced neurobehavioral effects: causal or concausal? A practical advice. *Daru.*, 23(1), p. 25. doi:10.1186/s40199-015-0109-6

Selvarajah, D., Gandhi, R., Emery, C. J., & Tesfaye, S. (2010, January). Randomized placebo-controlled double-blind clinical trial of *cannabis*-based medicinal product (Sativex) in painful diabetic neuropathy: depression is a major confounding factor. *Diabetes Care.*, 33(1), pp. 128-30. doi:10.2337/dc09-1029

Serpell, M., Ratcliffe, S., Hovorka, J., Schofield, M., Taylor, L., Lauder, H., & Ehler, E. (2014, August). A double-blind, randomized, placebo-controlled, parallel group study of THC/CBD spray in peripheral neuropathic pain treatment. *Eur J Pain*, 18(7), pp. 999-1012. doi:10.1002/j.1532-2149.2013.00445.x Svendsen, K. B., Jensen, T. S., & Bach, F. W. (2004, Jul. 31). Does the cannabinoid dronabinol reduce central pain in multiple sclerosis? Randomised double blind placebo controlled crossover trial. *BMJ*, 329(7460), p. 253. doi: 10.1136/bmj.38149.566979.AE Symonds, C., & Berman, J. (2003). US Patent No. US20060135599 A1.

Thomas, A., Baillie, G. L., Phillips, A. M., Razdan, R. K., Ross, R. A., & Pertwee, R. G. (2007, March). Cannabidiol displays unexpectedly high potency as an antagonist of CB1 and CB2 receptor agonists in vitro. *Br J Pharmacol.*, 150(5), pp. 613-23. doi: 10.1038/sj.bjp.0707133

Ungerleider, J. T., Andrysiak, T., Fairbanks, L., Ellison, G. W., & Myers, L. W. (1987). Delta-9-THC in the treatment of spasticity associated with multiple sclerosis. *Adv Alcohol Subst Abuse*, 7(1), pp. 39-50. Retrieved from https://www.ncbi.nlm.nih.gov/pubmed/2831701

Ungerleider, J. T., Andrysiak, T., Fairbanks, L., Ellison, G. W., & Myers, L. W. (1987). Delta-9-THC in the treatment of spasticity associated with multiple sclerosis. *Adv Alcohol Subst Abuse*, 7(1), pp. 39-50. doi:10.1300/J251v07n01_04

Vaney, C., Heinzel-Gutenbrunner, M., Jobin, P., & et al. (2004, August). Efficacy, safety and tolerability of an orally administered *cannabis* extract in the treatment of spasticity in patients with multiple sclerosis: a randomized, double-blind, placebo-controlled, crossover study. *Mult Scler.*, 10(4), pp. 417-24. doi:10.1191/1352458504ms1048oa Wade, D. T., Makela, P. M., House, H., & et al. (2006, October). Long-term use of a *cannabis*-based medicine in the treatment of spasticity and other symptoms in multiple sclerosis. *Mult Scler.*, 12(5), pp. 639-45. doi:10.1177/1352458505070618

Wade, D. T., Makela, P., Robson, P., & et al. (2004, August). Do *cannabis*-based medicinal extracts have general or specific effects on symptoms in multiple sclerosis? A double-blind, randomized, placebo-controlled study on 160 patients. *Mult Scler.*, 10(4), pp. 434-41. doi:10.1191/1352458504ms1082oa Wade, D. T., Robson, P., House, H., & et al. (2003, February). A preliminary controlled study to determine whether whole-plant *cannabis* extracts can improve intractable neurogenic symptoms. *Clin Rehabil.*, 17(1), pp. 21-9. doi:10.1191/0269215503cr581oa Ware, M. A., Wang, T., Shapiro, S., & et al. (2010, Oct. 5). Smoked *cannabis* for chronic neuropathic pain: a randomized controlled trial. *CMAJ*, 182(14), pp. E694-701. doi: 10.1503/cmaj.091414

Wilsey, B., Marcotte, T., Tsodikov, A., & et al. (2008, June). A randomized, placebo-controlled, crossover trial of *cannabis* cigarettes in neuropathic pain. *J Pain*, 9(6), pp. 506-21. doi: 10.1016/j.jpain.2007.12.010

Wissel, J., Haydn, T., Miller, J., & et al. (2006, October). Low dose treatment with the synthetic cannabinoid Nabilone significantly reduces spasticity-related pain: a double-blind placebo-controlled cross-over trial. *J Neurol.*, 253(10), pp. 1337-41. doi:10.1007/s00415-006-0218-8

Zajicek, J. (2007). US Patent No. US20080175902 A1.

Zajicek, J. P., Sanders, H. P., Wright, D. E., & et al. (2005, December). Cannabinoids in multiple sclerosis (CAMS) study: safety and efficacy data for 12 months follow up. *J Neurol Neurosurg Psychiatry*, 76(12), pp. 1664-9. doi: 10.1136/jnnp.2005.070136

Zajicek, J., Fox, P., Sanders, H., & et al. (2003, Nov. 8). Cannabinoids for treatment of spasticity and other symptoms related to multiple sclerosis (CAMS study): multicentre randomised placebo-controlled trial. *Lancet*, 362 (9395), pp. 1517-26. doi:10.1016/S0140-6736(03) 14738-1

Zuardi, A. W., Crippa, J. A., Hallak, J. E., Pinto, J. P., Chagas, M. H., Rodrigues, G. G., . . . Tumas, V. (2009, November). Cannabidiol for the treatment of psychosis in Parkinson's disease. *J Psychopharmacol*, 23(8), pp. 979-83. doi:10.1177/0269881108096519.

What claimed is:

1. A method of treating with reduced adverse psychotropic effect pain, inflammation, mood and motor symptoms associated with psychiatric, autoimmune and neurological diseases and disorders in a subject manifesting one or more of said symptoms, the method comprising administering to a subject 0.3 mg or more of a pharmaceutical compound one or more times in 24 hours, comprising of an extract of a *Cannabis* plant and at least one pharmacologically inactive substance; and where said extract contains one or more tetrahydrocannabinol (THC) isomers and one or more cannabidiol (CBD) isomers in the ratio of 1 (THC) and 2 (CBD) by mass; and where said CBD augments the pharmacodynamics of THC in a subject; and where said compound contains one or more non-cannabinoid components consisting of one or more of the following: terpenes; sterols; triglycerides; alkanes; squalene; tocopherol; carotenoids; chlorophyll; flavonoid; glycosides and alkaloids.

2. The method of claim 1, where said extract contains one or more tetrahydrocannabinol (THC) isomers and one or more cannabidiol (CBD) isomers in the ratio of 0.5 to 1 (THC) and 1.5 to 2 (CBD) by mass.

3. The method of claim 1, where said extract contains one or more tetrahydrocannabinol (THC) isomers and one or more cannabidiol (CBD) isomers in the ratio of 1 to 1.8 (THC) and 2 to 2.5 (CBD) by mass.

4. The method of claim 1, where said compound contains one or more other cannabinoids.

5. The method of claim 1, where said compound is administered in a sustained release, or extended release, or a combined sustained release, or extended release fraction dosage form, or in an immediate release dosage form, or a combined sustained release fraction and immediate release fraction dosage form, or a combination thereof.

6. The method of claim 1, where said compound is administered by a route selected from the group consisting of: oral, intranasal, inhalation, parenteral, transdermal, rectal, vaginal, buccal, and sublingual, or combination thereof.

7. The method of claim 1, where said compound is administered in a dosage form selected from the group consisting of: a tablet, a hard gelatin capsule, a soft gelatin capsule, a non-gelatin capsule, an HPMC capsule, an inhalant, an injectable, a transdermal, a buccal, a sublingual, and a rectal or a vaginal suppository.

8. The method of claim 1, where said treatment involves obtaining from the subject at least once in 72 hours at least some vital signs parameters.

9. The method of claim 1, where said compound is administered in combination with one or more other medications.

10. The method of claim 1, where said compound is administered for treating symptoms associated with diseases or disorders selected from the group consisting of: autoimmune diseases and disorders, motor neuron diseases and disorders, neurodegenerative diseases and disorders, pain associated with cancer and trauma.

11. The method of claim 1, where said tetrahydrocannabinol (THC) or said cannabidiol (CBD) is one or more of: (i) natural cannabinoids that have been purified or modified; (ii) synthetically derived cannabinoids; (iii) semi-synthetic cannabinoids; (iv) esterified cannabinoids; (v) active metabolites of any of the foregoing, (vi) pro-drugs of any of the foregoing; and (vii) mixtures thereof.

12. The method of claim 1, where said compound is a liquid solution or liquid suspension.

13. The method of claim 1, where said compound is administered for treating spasticity symptoms associated with multiple sclerosis disease or other neurodegenerative diseases.

14. A pharmaceutical compound for treating with reduced adverse psychotropic effect pain, inflammation, mood and motor symptoms associated with psychiatric, autoimmune and neurological diseases and disorders in a subject manifesting one or more of said symptoms, comprising of an extract of *Cannabis sativa* plant and at least one pharmacologically inactive substance; and where said extract contains one or more tetrahydrocannabinol (THC) isomers and one or more cannabidiol (CBD) isomers in the ratio of 1 (THC) and 2 (CBD) by mass; and where said CBD augments the pharmacodynamics of THC in a subject; and where said compound contains one or more non-cannabinoid components consisting of one or more of the following: terpenes; sterols; triglycerides; alkanes; squalene; tocopherol; carotenoids; chlorophyll; flavonoids; glycosides and alkaloids.

15. The compound of claim 14, where said extract contains one or more tetrahydrocannabinol (THC) isomers and one or more cannabidiol (CBD) isomers in the ratio of 0.5 to 1 (THC) and 1.5 to 2 (CBD) by mass.

16. The compound of claim 14, where said extract contains one or more tetrahydrocannabinol (THC) isomers and one or more cannabidiol (CBD) isomers in the ratio of 1 to 1.8 (THC) and 2 to 2.5 (CBD) by mass.

17. The compound of claim 14, where said compound contains one or more other cannabinoids, at least one of the following: cannabigerol (CBG), Cannabichromene (CBC), cannabinol (CBN), cannabielsoin (CBE), iso-tetrahydrocannabimol (iso-THC), cannabicyclol (CBL), cannabicitran (CBT), cannabivarin (CBV), tetrahydrocannabivarin (THCV), cannabidivarin (CBDV), cannabichromevarin (CBCV), cannabigerovarin (CBGV) and cannabigerol monomethyl ether (CBGM), or any combination thereof, or a natural or synthetic analogue thereof, and/or derivatives thereof.

18. The compound of claim 14, where said extract of *Cannabis sativa* is obtained by supercritical or subcritical extraction with CO2 or purified using chromatographic techniques.

19. The compound of claim 14, where said compound is packaged in a dosage form selected from the group consisting of: a tablet, a hard gelatin capsule, a soft gelatin capsule, a non-gelatin capsule, an HPMC capsule, an inhalant, a parenteral, a transdermal, a sublingual, a rectal, a vaginal, and a suppository.

20. The compound of claim 14, where said pharmacologically inactive substance contains at least some sesame oil, or its derivative, or pharmaceutically acceptable fixed oil.

21. The compound of claim 14, where said compound contains one or more other medications.

22. The compound of claim 14, where said compound is used for treating symptoms associated with diseases or disorders selected from the group consisting of: autoimmune diseases and disorders, motor neuron diseases and disorders, neurodegenerative diseases and disorders, pain associated with cancer and trauma.

23. The compound of claim 14, where said tetrahydrocannabinol (THC) or said cannabidiol (CBD) is one or more of: (i) natural cannabinoids that have been purified or modified; (ii) synthetically derived cannabinoids; (iii) semi-synthetic cannabinoids; (iv) esterified cannabinoids; (v) active metabolites of any of the foregoing, (vi) pro-drugs of any of the foregoing; and (vii) mixtures thereof.

24. The compound of claim 14, where said compound is a liquid solution or liquid suspension.

25. The compound of claim 14, where the initial purity of said tetrahydrocannabinol (THC) or said cannabidiol (CBD) by HPLC is at least 98% by area and the stability is such that at least 95% by area remains in undegraded form after exposure of the compound to the storage conditions for at least twelve months, where the ambient temperature is between 20° C. and 40° C. and relative humidity is between 55% and 75%.

26. The compound of claim 14, where said compound is used for treating spasticity symptoms.

27. A pharmaceutical compound for treating with reduced adverse psychotropic effect pain, inflammation, mood and motor symptoms associated with psychiatric, autoimmune and neurological diseases and disorders in a subject manifesting one or more of said symptoms, comprising of an extract of one or more *Cannabis* species plants and at least one pharmacologically inactive substance; and where said compound is packaged in a soft gelatin capsule, where said capsule does not contain lambda-carrageenan, kappa-carrageenan, iota-carrageenan and any mixture of the carrageenans.

* * * * *